(12) United States Patent
Gerber et al.

(10) Patent No.: US 9,764,073 B2
(45) Date of Patent: Sep. 19, 2017

(54) AUTHENTICATION AND TRACKING SYSTEM

(71) Applicant: Medtronic, Inc., Minneapolis, MN (US)

(72) Inventors: Martin T. Gerber, Maple Grove, MN (US); Venkatesh R. Manda, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 14/261,751

(22) Filed: Apr. 25, 2014

(65) Prior Publication Data
US 2015/0238673 A1 Aug. 27, 2015

Related U.S. Application Data

(60) Provisional application No. 61/945,095, filed on Feb. 26, 2014.

(51) Int. Cl.
| | | |
|---|---|---|
| *A61M 1/14* | (2006.01) | |
| *A61M 1/16* | (2006.01) | |
| *G06K 19/077* | (2006.01) | |

(52) U.S. Cl.
CPC .............. *A61M 1/14* (2013.01); *A61M 1/16* (2013.01); *A61M 1/1696* (2013.01); *G06K 19/077* (2013.01); *A61M 2205/18* (2013.01); *A61M 2205/3561* (2013.01); *A61M 2205/3569* (2013.01); *A61M 2205/3592* (2013.01); *A61M 2205/6009* (2013.01); *A61M 2205/6054* (2013.01); *A61M 2205/6063* (2013.01)

(58) Field of Classification Search
None
See application file for complete search history.

(56) References Cited

U.S. PATENT DOCUMENTS

| | | | |
|---|---|---|---|
| 6,468,424 | B1 | 10/2002 | Donig |
| 6,685,831 | B2 | 2/2004 | Donig |
| 7,755,488 | B2 | 7/2010 | Dvorsky |
| 7,955,295 | B2 | 6/2011 | Lee |
| 8,496,609 | B2 | 7/2013 | Childers |
| 2001/0040127 | A1 | 11/2001 | Donig |

(Continued)

FOREIGN PATENT DOCUMENTS

| | | |
|---|---|---|
| CN | 103037917 | 4/2013 |
| EP | 0341799 | 11/1989 |

(Continued)

OTHER PUBLICATIONS

Office Action in U.S. Appl. No. 14/838,112 Dated Sep. 16, 2016.

(Continued)

*Primary Examiner* — Richard Gurtowski
(74) *Attorney, Agent, or Firm* — Kenneth Collier; Roger Hahn

(57) ABSTRACT

A dialysis authentication system comprising at least one dialysis component having at least one authentication component affixed thereon. The dialysis component can be any one of a dialyzer, sorbent cartridge, or recharger. The authentication component can be selected from the group comprising a radio-frequency identification marker, a bar code, a one-wire security component, and a wireless authentication component.

34 Claims, 24 Drawing Sheets

(56) References Cited

U.S. PATENT DOCUMENTS

| | | |
|---|---|---|
| 2002/0188259 A1 | 12/2002 | Hickle |
| 2009/0009290 A1 | 1/2009 | Kneip |
| 2009/0012448 A1 | 1/2009 | Childers |
| 2009/0012449 A1 | 1/2009 | Lee |
| 2009/0069925 A1 | 3/2009 | Dattolo |
| 2009/0079578 A1 | 3/2009 | Dvorsky |
| 2009/0275883 A1 | 11/2009 | Chapman |
| 2009/0289796 A1 | 11/2009 | Blumberg |
| 2009/0295659 A1 | 12/2009 | Blumberg |
| 2011/0017665 A1* | 1/2011 | Updyke ............. A61M 1/1696 210/638 |
| 2011/0048101 A1 | 3/2011 | Heide |
| 2011/0205134 A1 | 8/2011 | Blumberg |
| 2011/0209212 A1 | 8/2011 | Newlin |
| 2013/0062265 A1 | 3/2013 | Balschat |
| 2013/0175373 A1 | 7/2013 | Morgan |
| 2014/0027380 A1 | 1/2014 | Childers |
| 2015/0238673 A1 | 8/2015 | Gerber |
| 2015/0359954 A1 | 12/2015 | Gerber |

FOREIGN PATENT DOCUMENTS

| | | |
|---|---|---|
| EP | 2247926 B1 | 4/2012 |
| EP | 1449548 B1 | 1/2014 |
| EP | 2258419 B1 | 1/2014 |
| WO | 2012120078 A2 | 9/2012 |
| WO | 2014121909 | 8/2014 |
| WO | WO 2014121909 | 8/2014 |

OTHER PUBLICATIONS

Office Action in Chinese Application No. 201510086368.9, Dated Oct. 16, 2016.

International Search Report from PCT/US2015/015205 mailed Apr. 23, 2015.

Written Opinion in App. No. PCT/US2016/048814 dated Jan. 17, 2017.

* cited by examiner

AUTHENTICATION AND TRACKING SYSTEM

The present application claims benefit to provisional application No. 61/945,095, filed Feb. 26, 2014; which is hereby incorporated-by-reference.

FIELD OF THE INVENTION

The present invention relates to an authentication, identification and tracking system for use with a dialysis system. The dialysis components can be detachable and/or reusable. The dialysis components can have connectors in fluid communication with a dialysis flow path or circuit. The present invention can also be used to manage reprocessing of sorbent materials and to ensure the pairing of a dialysis component with a specific patient thereby mitigating the risk of transfer of infectious disease. The present invention can also authenticate dialysis components to eliminate counterfeits and manage product features such as number of recharges and expiration date, among others.

BACKGROUND

Individual components of a dialysis system must work together properly. In general, specific components can be designed by a manufacturer to be utilized with other specific components. The manufacturer of one component may also manufacture other components of a dialysis system, or may certify that these other components can be used with the manufacturer's own components (hereinafter collectively referred to as a "certified product"). When one of the components being used is not a certified product, the full capabilities of the system may not be achieved. Further, use of non-certified products may cause malfunctions, endangering patient safety. Patient safety can likewise be endangered by cross-usage of dialysis components. Certain components should only be used by a specific patient in order to avoid contamination. Use of the reusable components of a dialysis system beyond their useful life can also cause malfunctions and a decrease in effectiveness.

Dialysis involves the movement of blood through a dialyzer that has a semi-permeable membrane. Simultaneously, dialysate is circulated through the dialyzer on an opposite side of the semi-permeable membrane. Toxins present in the blood stream of the patient pass from the blood through the membrane into the dialysate. After passing through the dialyzer, the spent dialysate is discarded. Disposal of spent dialysate requires a large amount of source water for preparing the replacement dialysate necessary for use during continuous dialysis. However, in sorbent dialysis systems, the spent dialysate is re-circulated through a sorbent cartridge rather than being discarded. The sorbent cartridge contains layers of sorbent material which selectively remove specific toxins, or break down toxins, in the dialysate. As such, sorbent dialysis requires a much lower amount of water. In four hours of traditional dialysis, up to 120 L of water may be required to generate the dialysate. By contrast, using sorbent dialysis, as little as 6 or 7 L of water may be necessary. Thus, the need for drains and a continuous source of purified water are eliminated, rendering the system portable.

One of the drawbacks of sorbent dialysis systems is the high cost. The materials used in the sorbent cartridges can be expensive. Disposing of the cartridges after each use generates waste and drives up costs. Regeneration of some or all of the components of a sorbent cartridge will allow for reuse of these components and will lower long-term costs.

Separation of some of the materials within the sorbent cartridge into separate modules may allow for isolation of those materials. Isolation of the material allows for cheaper or non-reusable materials to be discarded, while more expensive and reusable materials can be regenerated.

Hence, there is a need for separating the sorbent cartridge into multiple discreet modules that can be easily connected and thereby facilitate the regeneration and/or recycling of the sorbent materials and the sorbent cartridge. There is also a need for identification of the specific components of a dialysis system and for a modular sorbent cartridge with detachable components or parts. There is a further need for a system by which reusable components of a dialysis system may be certified such that the components are shown to be the manufacturer's own components or alternatively a "certified product." There is also a need for determining when a component used during dialysis, such as a reusable component, is or is not the manufacturer's certified product. There is a need for preventing non-certified products from being used in a particular system to avoid malfunctions and avoid endangering patient safety. There is also a need for preventing cross-usage of dialysis components between different patients or sessions. There is a need for preventing reusable components of a dialysis system from being used beyond their useful life. There is also a need to ensure that reusable components of a dialysis system are properly returned to their initial states before being reused.

There is also a need for tracking components in order to ensure that the components are certified components, that the components are being used by the correct patients, and that the components have not outlived their useful lives. There is a need for a system by which individual reusable modules of a modular sorbent cartridge are tracked to ensure that they are certified components, that they contain the correct sorbent materials, that they are being used by the correct patients, and that they have not been used beyond their useful lives.

SUMMARY OF THE INVENTION

The invention is directed to a dialysis authentication system for use in dialysis that includes at least one dialysis component having at least one authentication component affixed thereon.

In one embodiment, the dialysis component can be any one of a dialyzer, sorbent cartridge or recharger.

In one embodiment, the dialysis component can be a sorbent cartridge comprising at least one reusable module.

In another embodiment, the sorbent cartridge can have one or more connectors fluidly connectable with a fluid flow path or to a second component.

In another embodiment, the reusable module can be detachable.

In another embodiment, the authentication component can be selected from a group comprising a radio-frequency identification marker (RFID tag), a barcode, a one-wire security component, and a wireless authentication component.

In another embodiment, the dialysis authentication system can further comprise a memory device.

In another embodiment, the dialysis authentication system can further comprise a reader to read the authentication component.

In another embodiment, the dialysis authentication system can further comprise a writer to write to the authentication component.

In another embodiment, the sorbent cartridge can further comprise at least one valve positioned before and/or after the module on the connectors to selectively direct flow through any one of a module, a wash line, a recharger, or a bypass line.

In another embodiment, the sorbent cartridge can further comprise any one of a four-way, three-way, or two-way valve, or combinations thereof, positioned before and/or after the module on the connectors to selectively direct fluid flow through any one of a module, a wash line, a recharger, or a bypass line.

In another embodiment the authentication component affixed to the dialysis component can be any one of a bar code, a radio-frequency identification marker, a one-wire security component, or a wireless authentication component.

In another embodiment, the authentication component can have a dialysis component-specific unique identifier.

In another embodiment, the authentication component can have a manufacturer-specific unique identifier.

In another embodiment, the system can further comprise a processor for correlating the dialysis component-specific unique identifier with the manufacturer-specific unique identifier.

In another embodiment, the authentication component can have a user-specific unique identifier.

In another embodiment, the system can further comprise a processor for correlating the dialysis component-specific unique identifier with the user-specific unique identifier.

In another embodiment, the dialysis authentication system can have a processor for monitoring the usage of the dialysis component.

In another embodiment, the processor can monitor the number of times the dialysis component is disconnected and reconnected to the system.

In another embodiment, the processor can monitor the contents of the dialysis component.

In another embodiment, the processor can monitor a length of time between uses of the dialysis component.

In another embodiment, the authentication component can detect the usage of a counterfeit dialysis component.

In another embodiment, the authentication component can disable the usage of a counterfeit dialysis component.

In another embodiment, the dialysis authentication system can further comprise a memory device that can track the dialysis component to determine the product history of the dialysis component.

In another embodiment, the authentication component can be built into the dialysis component.

In another embodiment, the dialysis authentication system can comprise more than one reader.

In another embodiment the memory component can be integrated with the authentication component.

In another embodiment, the memory component can be separate from the authentication component.

In another embodiment, the memory component can comprise a database to track multiple dialysis components.

In another embodiment, the dialysis component can be a sorbent.

In another embodiment, the authentication component can be placed inside the sorbent.

In another embodiment, the dialysis authentication system can further comprise a wireless network to track the authentication component.

In another embodiment the wireless network can utilize any wireless protocol. In certain embodiments, the wireless protocol can be any one of WiFi, LTE, Bluetooth or WiMax. In other embodiments, the wireless protocols can be any wireless protocol including a proprietary protocol.

In another embodiment, the system can determine how many times the dialysis component has been used.

In another embodiment, the system can alert a user if the dialysis component has been used more than a pre-set number of times.

In another embodiment, the authentication component can have an expiration date corresponding to the dialysis component to which the authentication component is affixed.

In another embodiment, the system can alert a user if the dialysis component has reached an expiration date of the dialysis component.

In another embodiment, the authentication component can include information on whether or not the dialysis component has been recharged.

In another embodiment, the dialysis component can be a single use component and the authentication component can include information on whether the dialysis component has been previously used.

In another embodiment, the authentication component can contain information on the date the dialysis component was last used.

In another embodiment, the dialysis authentication system can alert a user if the length of time between uses of the dialysis component is greater than a pre-set length of time.

In another embodiment, the memory device can track performance data of the dialysis component.

In another embodiment, the authentication component can require electrical contact with the reader for the authentication component to communicate with the reader; and a spring can be placed on the dialysis component such that when the dialysis component is attached in a fluid flow path, the spring causes the authentication component to come into electrical contact with the reader.

The invention is also directed to a recharger comprising a recharger and at least one authentication component affixed thereon.

The invention is also directed to a dialyzer comprising a dialyzer and at least one authentication component affixed thereon.

The invention is also directed to a method for identifying a dialysis component having at least one authentication component affixed thereon. The method can comprise the steps of connecting a dialysis component having at least one authentication component affixed thereon to a system capable of identifying the dialysis component and identifying a dialysis component by associating an identifier with the authentication component wherein the authentication component receives a signal from the identifier and in response to the signal emits a response signal to a detector which identifies the dialysis component.

In another embodiment, the dialysis component can be any one of a sorbent cartridge, a dialyzer or a recharger.

In another embodiment, the method can further comprise obtaining a patient-specific unique identifier and utilizing a processor in electronic communication with the detector to determine if the dialysis component is matched to a patient.

In another embodiment, the dialysis component can be a single use component and the method can further comprise the step of utilizing a processor in electronic communication with the detector to determine if the dialysis component has been previously used.

In another embodiment, the method can include utilizing a processor in electronic communication with the detector to determine if the dialysis component is a certified component.

In another embodiment, the dialysis component can be a rechargeable component.

In another embodiment, the method can further comprise utilizing a processor in electronic communication with the detector to determine if the dialysis component has been recharged.

In another embodiment, the method can further comprise utilizing a processor in electronic communication with the detector to determine if the dialysis component has been recharged more than a pre-set number of times.

In another embodiment, the system can be capable of tracking the use of the dialysis component, and the method can further comprise the step of entering the date of use of the dialysis component after the dialysis component is used.

DETAILED DESCRIPTION OF THE INVENTION

Figure 1:
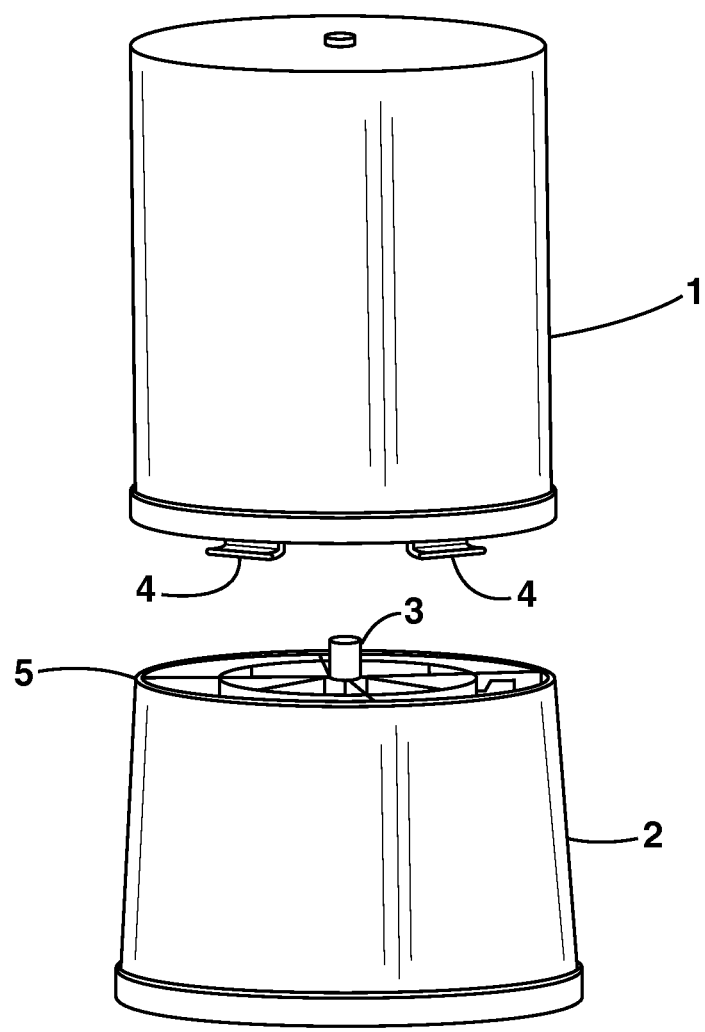
FIG. 1 shows a modular sorbent cartridge having two modules.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "antenna" is a component capable of sending or receiving electromagnetic waves.

The terms "authentication component" or "identification component" may be used interchangeably, and refer to a component that allows for identification of a particular component to which the authentication component is attached.

A "bar code" is a computer readable pattern of parallel lines and spaces of variable thickness that identifies the component to which the barcode is attached.

"Blow out" refers to the process of passing a gas through a connection line or a module.

"Bypass line" refers to a line, connected to the main line, through which fluid or gas may alternatively flow.

The term "cartridge" refers to any container designed to contain a powder, liquid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "cation concentrate reservoir" refers to an object having or holding a substance that is comprised of at least one cation, for example, calcium, magnesium, or potassium ions.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid; non-limiting examples can be glucose, dextrose, acetic acid and citric acid.

A "certified product," "certified component" or "certified part" is a component of a dialysis system wherein the manufacturer of the other components of the dialysis system has determined that the component is certified. In some cases, certification can indicate that the component is capable of being safely and effectively used in the system.

The term "comprising" includes, but is not limited to, whatever follows the word "comprising." Thus, use of the term indicates that the listed elements are required or mandatory but that other elements are optional and may or may not be present.

A "connector" as used herein forms a fluid connection between two components wherein liquid or gas can flow from one component, through the connector, to another component. It will be understood that the connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "container" as used herein in the context of a controlled compliant circuit is a receptacle that may be flexible or inflexible for holding any fluid or solid, such as for example a spent dialysate fluid, or a sodium chloride or sodium bicarbonate solution or solid, or the like.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, the controlled compliant system can move fluids bi-directionally. In certain cases, the bi-directional fluid movement can be across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "controller," "control unit," "processor," or "microprocessor" is a device which monitors and affects the operational conditions of a given system. The operational conditions are typically referred to as output variables of the system wherein the output variables can be affected by adjusting certain input variables.

A "control valve" is a valve for controlling the movement of a liquid or a gas. When the control valve directs the movement of gas, the "control valve" can open or close to regulate movement of gas from a high pressure gas source to a lower pressure.

A "degasser" is a component that is capable of removing dissolved and undissolved gasses from fluids.

The term "detachable" or "detached" relates to any component of the present invention that can be separated from a system, module, cartridge or any component of the invention. "Detachable" can also refer to a component that can be taken out of a larger system. In certain instances, the components can be detached with minimal time or effort, but in other instances can require additional effort. The detached component can be optionally reattached to the system, module, cartridge or other component. A detachable module can often be part of a reusable module.

A "detector" is a device for receiving digital information sent from the antenna on the authentication component.

"Dialysate" is the fluid that passes through the dialyzer and does not pass through the membrane into the blood flow.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis component" is any component that is designed to be used for dialysis or as a part of a dialysis system.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

The term "extracorporeal circuit" or "extracorporeal flow path" refers to a fluid pathway incorporating one or more components such as but not limited to conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

"Flow" refers to the movement of a liquid or gas.

A "flow sensing apparatus" or "flow measuring apparatus" is an apparatus capable of measuring the flow of liquid or gas within a specific area.

A "fluid" is a liquid substance.

The term "fluid communication" refers to the ability of fluid or gas to move from one component or compartment to another within a system or the state of being connected, such that fluid or gas can move by pressure differences from one portion that is connected to another portion.

The term "fluidly connectable" refers to the ability of providing for the passage of fluid or gas from one point to another point. The two points can be within or between any one or more of compartments, modules, systems, components, and rechargers, all of any type.

The term "identifying information" refers to information about a component or class of components. Identifying information can refer to information that identifies the particular component in question, information that identifies the type of component, or information that identifies the manufacturer of the component.

"Infusate" is a solution of one or more salts for the adjustment of the composition of a dialysate.

The term "in-line" refers to a state in which a module or set of modules is fluidly connected to a dialysis machine, dialysis flow path or dialysis circuit. Dialysis can be on-going, paused or stopped during the in-line state wherein in-line only refers to the state of the modules being fluidly connected to the dialysis machine, dialysis flow path or dialysis circuit.

"Memory" is a device capable of storing digital information on a temporary or permanent basis.

A "memory device" is a device for recording digital information that can be accessed by a microprocessor, such as RAM, Dynamic RAM, microprocessor cache, or Flash memory.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. It will be understood that the designation of "first," "second," "third," etc. does not refer to the respective placement of the module in the direction of fluid or gas flow, and merely serves to distinguish one module from another unless otherwise indicated.

The term "non-reusable" refers to a component that cannot be reused in the component's current state. In certain instances, the term non-reusable can include the concept of being disposable, but is not necessarily limited to just being disposable.

The term "off-line" refers to a state in which a module or set of modules is fluidly disconnected from a dialysis machine, dialysis flow path or dialysis circuit. Dialysis can be on-going, paused or stopped during the off-line state wherein off-line only refers to the state of the modules being fluidly disconnected from the dialysis machine, dialysis flow path or dialysis circuit. The off-line state can also include a process whereby the module or set of modules is being recharged as defined herein.

A "one-wire security component" is a component comprising two parts that can be connected by a wire, wherein the first part sends an identification signal to the second part, and then the second part sends a unique identification signal back to the first part, with both transmissions occurring over the same wire. Although the term wire is used, any type of contact between one or more surfaces sufficient to provide for transmission of an electrical signal between the two surfaces is also encompassed by the invention. For example, two plates in electrical contact can be considered to be connected by a wire.

An "operational line" or "line" is a passageway, conduit or connector that directs fluid or gas in a path used while the system is in operation.

The terms "pathway," "conveyance pathway," "fluid flow path," and "flow path" refer to the route through which a fluid or gas, such as dialysate or blood travels, or the route an inert gas travels.

The terms "pressure meter" and "pressure sensor" refer to a device for measuring the pressure of a gas or liquid in a vessel or container.

A "pressure valve" is a valve wherein, if the pressure of the fluid or gas passing the valve reaches a certain level, the valve will open to allow fluid or gas to pass through.

A "processor" is a device which monitors and affects the operational conditions of a given system. The operational conditions are typically referred to as output variables of the system, which can be affected by adjusting certain input variables.

"Product history" refers to any one or combination of features related to the product for the use, type of use, time of use, origin, manufacturer, components, user, and any other but not necessarily limited to, time-dependent data of the product.

The term "pump" refers to any device that causes the movement of fluids or gases by the application of suction or pressure.

A "push-on fitting" is a fitting for connecting two components wherein the components may be connected by applying pressure to the base of the fitting attached to the components.

A "quick connect fitting" is a fitting for connecting two components wherein the male portion of the fitting contains flexible flanges extending outward with a portion on the end of the flange extending further outward, and the female portion of the fitting contains an internal ridge so that when connected, the outward extending portion of the flange sits under the ridge. By applying pressure, the flexible flange can be forced inward, past the ridge, enabling easy removal.

"Radio Frequency Identification," "RFID" or "RFID tag" refers to a device capable of transmitting radio frequency signals to a receiver for identification.

A "reader" is a component that is capable of receiving information from an RFID tag, one-wire security component or wireless authentication component, or by scanning a bar code.

A "recharger" is a component that is capable of recharging spent sorbent material to or near its original state. A recharger may be part of the dialysis system, or may be separate from the rest of the system. If the recharger is separate from the rest of the dialysis system, the term may include a separate facility where the spent sorbent material is sent to be returned to, or near, its original state.

"Recharging" refers to the process of treating spent sorbent material so as to put the sorbent material back in condition for use in sorbent dialysis. Upon a sorbent material undergoing "recharging," the sorbent material can then said to be "recharged."

The term "recyclable" refers to a material that can be reused.

"Reusable" refers in one instance to a sorbent material that can be used more than one time, possibly with treatment or recharging of the sorbent material between uses. Reusable may also refer to a sorbent cartridge that contains a sorbent material that can be recharged by recharging the sorbent material(s) contained within the sorbent cartridge.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Sorbent materials" are materials that are capable of removing specific solutes from solution, such as urea.

"Spent dialysate" is a dialysate contacted with blood through a dialysis membrane and contains one or more impurity, or waste species, or waste substance, such as urea.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

A "twist-lock fitting" is a fitting for connecting two components wherein the male portion of the fitting contains a head with a length exceeding its width, the female portion of the fitting is a hole with a length that exceeds its width and is larger than the male portion, so that when the male portion is inserted into the female portion and either portion is twisted the two components become locked together.

A "unique identifier" is information stored in an authentication component that is capable of distinguishing one component from other components of the same type.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

A "wash line" is a line that directs fluid between a recharger and a module.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The terms "waste species," "waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "water source" refers to a source from which potable or not potable water can be obtained.

A "wireless authentication component" is an authentication component that transmits identification information to a receiver without being directly connected to the receiver.

A "writer" is a component that is capable of transmitting digital information to a reader.

Dialysis Authentication System

In a dialysis system where some or all of the components are detachable and/or reusable, the correct components must be assembled before use. Further, for reusable components, tracking the usage of these components is important to ensure that the components are not being used beyond their useful lives. Patient safety likewise depends on avoiding cross-patient usage of certain components. Deterring counterfeiting, theft, tax avoidance, illegal importation and loss of inventory during use of the system are likewise important.

An example of a sorbent cartridge that includes a detachable, reusable module is shown in FIG. 1. A reusable module 1 can be fluidly attached to a non-reusable module 2 by a connector 3 with the use of latch members 4 disposed near the circumference of the reusable module 1. The latch members 4 can be integrally formed as part of the reusable module 2, or may be a separate component that can be attached to the module 2. The latch members 4 can be mated to an annular connection ring 5 disposed on the circumference of module 2. One or more engagement members can be disposed inside the annular connection ring 5 to engage the latches 4 when positioned relative to each other using a radial motion. Such engagement can cause a rigid connection between the reusable module 1 and the non-reusable module 2. Other known locking or fastening mechanisms known to those of ordinary skill that can effectuate rapid and effective connections between two components are contemplated by the invention. Although only cylindrical modules are shown, it will be understood that modules of any shape such as rectangular, conical, triangular, etc. are contemplated by the present invention with a correspondent fastening mechanism. The connector 3 can be formed as part of the reusable module 1 and the non-reusable module 2 and need not be a separate component that must be attached to the module 2. Rather, the connector 3 can be molded as part of the reusable module 1 and the non-reusable module 2. In other embodiments, the connector can be affixed by mechanical means, glued or rigidly interfaced to the modules 1 and 2. The connector can be a combination of female and male connectors on a module. For example, a female connector can be disposed on one module, and a male connector on the other to form one connector 3 (not shown). In any embodiment, the connector 3 allows fluid to flow from the non-reusable module 2, through the connector 3, into the reusable module 1. Alternatively, the connector 3 is not a part of either the non-reusable module 2 or reusable module 1 but can be a separate component such as tubing. It will be understood that the connector 3 is defined in its broadest sense and encompasses any fluid connection between two points.

After dialysis, the non-reusable module 2 may be detached from the reusable module 1. The material within the reusable module 1 may be recharged, the module may be emptied and refilled with new material, or alternatively the module may be discarded. In some embodiments, both modules of the two-module system may be reusable and/or detachable. In other embodiments, more than two modules may be used. Systems with 3, 4, or more modules are contemplated. Any of the modules may be detachable and/or reusable. The modules can be standardized components that are interchangeable with other modules and easily assembled. For example, the latches 4 in FIG. 1 allow for a simple, twist-lock between two modules. The twist lock allows for the modules to be connected to each other by an easy and rapid manual motion not requiring complex maneuvering of the modules. The connection, once made, can be resistant to inadvertent disengagement, but can also be readily disengaged when desired with a similar easy and rapid manual manipulation. For example, a force applied on the outside periphery of the modules near the latch, e.g. squeezing the module, can cause the latch member 4 to disengage from the engagement members. In other examples, the modules can be disengaged by simply rotating the modules relative to each other.

In certain embodiments, each module can function as a sorbent cartridge independently. In other embodiments, at least two modules can cooperate together when engaged to each other using, for example the latches 4 in FIG. 1 and being fluidly connected together to function as a sorbent cartridge. The advantage of such a modular design as described herein is that different sorbent materials can be dispersed between the at least two modules to allow for any particular sorbent or combination of sorbent materials to be detachable from a sorbent cartridge.

In sorbent dialysis, detachable modules within sorbent cartridges allow for replacement and/or regeneration of these modules. Providing a unique identifier to each of these components, and to the patient, will allow the patient to be certain that the correct components are assembled together, that the correct dialysis system is given to the correct patient, and that all of the components are authentic and not counterfeit.

In any embodiment, one or more fluid connectors can be arranged between any module of the invention, and one or more such fluid connectors can be provided in any of the described configurations herein. For example, a reusable or non-reusable module can have any number of connectors such as 1, 2, 3, 4, 5, or more. The spacing and distribution of the fluid connectors on the module can be positioned to enable and or increase flow of fluid between the modules. In one example, the fluid connectors can be spaced equidistant from each other or may be located axially or radially. The sorbent cartridge can also have one or more modules each having any number of fluid connectors. In contrast to known sorbent cartridges having a unitary design in which sorbent materials are arranged in layers without any connectors between such layers, the fluid connectors of the present invention allow for controlled fluid or gas flow to any particular sorbent or combination of sorbent materials. The fluid connectors also allow for any particular sorbent or combination of sorbent materials to be detachable from a sorbent cartridge. For example, a detachable module can be constructed with one or more sorbent materials. The detachable module can then be fluidly connected to the sorbent cartridge by fluid connectors. Such a configuration advantageously allows for separate treatment, recycling, or recharging of the sorbent or combination or mixture of sorbent materials not possible with known sorbent cartridges. In particular, known sorbent cartridges have all the sorbent materials being formed into layers or a plurality of sorbent materials being mixed without connectors in between such layers of one sorbent material, or mixtures of sorbent materials. It will be understood that the fluid connectors of the invention can be critical because the connectors control the order of sorbent materials to which a fluid or gas is exposed, the delivery of fluid or gas to a particular sorbent or combination of sorbent materials, and the flow and rate of flow of a fluid or gas to various sorbent materials, layers of sorbent materials, and combination or mixtures of sorbent material.

In one aspect of the invention, it will be understood that the present invention contemplates at least two modules that fit together, which is distinct from known dialysis systems having separate housings containing sorbent materials that do not form a unitary sorbent cartridge for ready attachment or insertion into a dialysis machine. A unitary sorbent cartridge of the present invention contains one or more of the sorbent materials described herein. In some embodiments, the cation and anion exchange materials necessarily reside in the sorbent cartridge. In other words, the cation and anion exchange resins (or other sorbent materials) are not separated into different housings outside a sorbent cartridge. Although the individual sorbent materials of the present invention may be separated into different detachable and/or reusable modules within the single sorbent cartridge wherein each module is connected by fluid connectors, the single sorbent cartridge design provides reduced size and weight that is not possible with the known dialysis systems having separate housings. The modules, as described herein, can also be further rigidly fixed to each other by latches and engagement members or any fixing or fastening mechanism known to those of ordinary skill in the art. Notably, the sorbent cartridge of the present invention can have all of the sorbent materials described herein including cation and anion exchange resins within a single unitary sorbent cartridge for convenient removal, service and monitoring. In particular, the sorbent cartridge can have a single compartmental design wherein all sorbent materials necessary for performing dialysis are contained within a single compartment. The sorbent cartridge can also have a modular design wherein the sorbent materials are dispersed across at least two different modules, which can be connected to form a unitary body. Once the at least two modules are connected together, the connected modules can form a sorbent cartridge to be fitted to a device or mechanism. Advantageously, the present sorbent cartridge can therefore be easier to recycle, recharge, dispose of, service and remove from a dialysis machine. In certain embodiments, the unitary design can also provide for a compact design that can be used in a portable dialysis machine. Further, manufacturability is benefited by the unitary design.

In any embodiment, the fluid connector can be a quick-connect, twist-lock fitting, push-on fitting, or threaded fitting. Other forms of such connection known to those of ordinary skill in the art are also contemplated by the present invention. Additionally, the connector can comprise a length of tubing and valve or a valve assembly. In certain embodiments, the connector can be manually assembled to connect any component or assembly of the invention. The connector can also be used to rigidly connect any one of the modules to a recharger as defined herein when a separate fastening mechanism is not provided.

Figure 2:
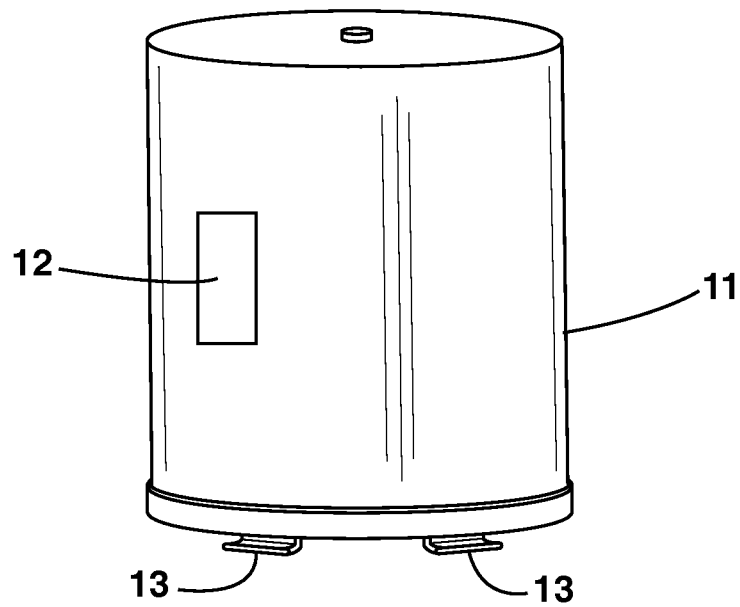
FIG. 2 shows a module with an identification component.

In order to ensure that the detachable components of the system are certified components, an identification component 12 may be affixed to or integrated with a detachable module 11, as shown in FIG. 2. The identification component 12 may be a bar code, RFID tag, one wire security component including electrical contact between one or more surfaces, or wireless authentication component, along with other identification components known to those skilled in the art. Alternatively, the identification component can be placed within the sorbent material itself. In such an embodiment, the identification component must work wirelessly, such as with an RFID component. The detachable module 11 can have latches 13 placed on circumference of the module 11 in order to facilitate attaching the module to a second module or other component.

Figure 3:
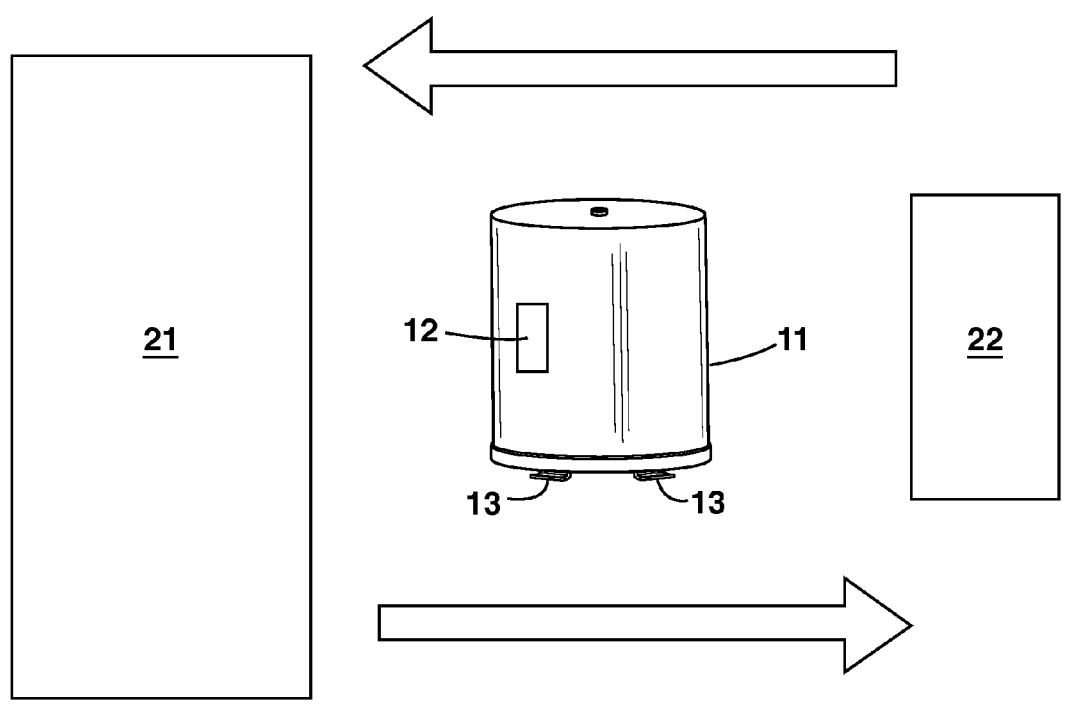
FIG. 3 shows one example of module tracking using an identification component.

FIG. 3 shows an example of the identification component in use. When the reusable module 11 is initially manufactured the module can have identification component 12 either affixed to the module or integrated within the module. It will be expressly understood that the dialysis component can also be any of a recharger, dialyzer or other component used for dialysis such as a bubble detector, pump, reservoir, bicarbonate cartridge among others. In addition to managing the reprocessing of sorbent materials, the present invention can be used to ensure the pairing of any specific dialysis component with a specific patient thereby mitigating the risk of transfer of infectious disease. Further, the present invention can also authenticate dialysis components to eliminate counterfeits and manage product features such as number of recharges, expiration date among others.

In any embodiment, the dialysis component can be detachable. If the dialysis component is a sorbent cartridge, the cartridge itself may have one or more modules that can be detachable. The reusable module 11 may also have latches 13 for attachment to a non-reusable module, or other component. After dialysis is complete, the patient 22 may send the reusable module 11 to a recharging facility represented by block 21 to have the materials within the module recharged. Depending on the facility, the reusable module 11 can optionally be recycled, replaced, recharged, or discarded. The identification component 12 allows tracking of the module 11 both at the block 21 and the patient 22. In this way, the company or person performing the recharging, recycling, replacing or discarding of the sorbent materials in block 21 can be assured that the reusable module 11 received is a certified product. Similarly, the patient 22 can be assured that the recycled module 11 received is the correct certified product.

Figure 4:
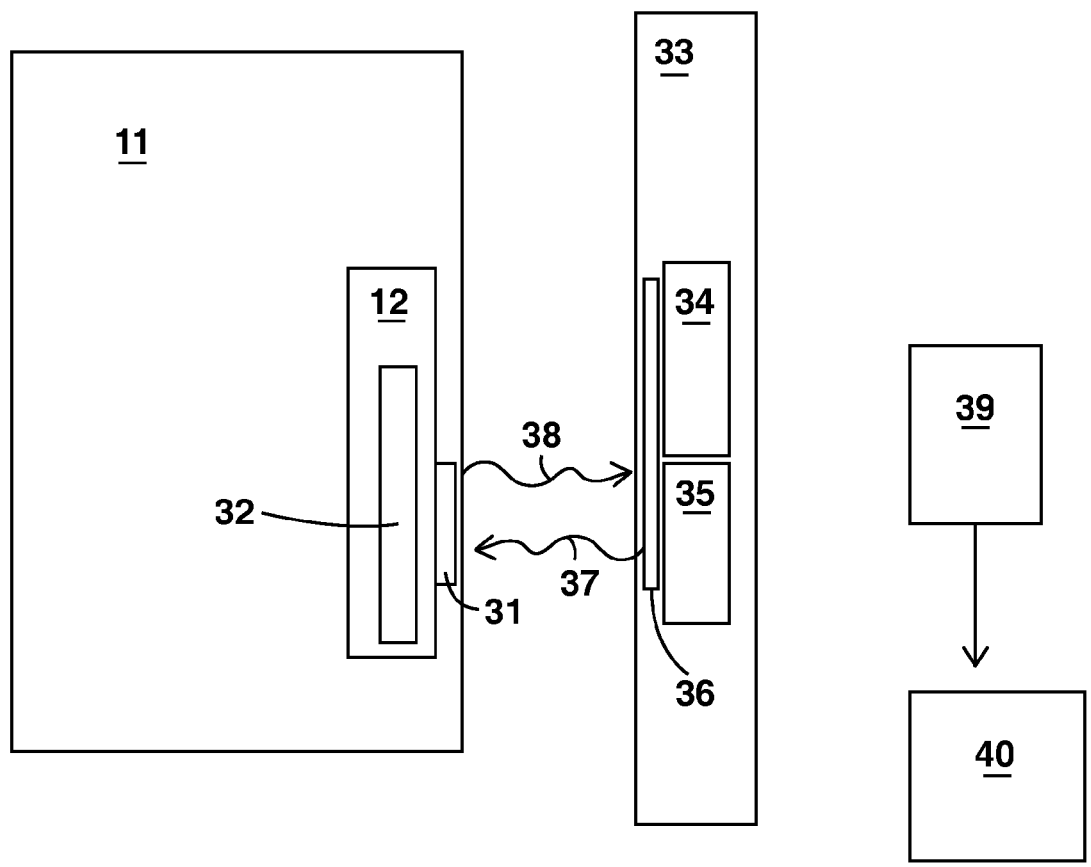
FIG. 4 shows an RFID identification component.

FIG. 4 shows a sample system wherein the identification component is an RFID component. The RFID tag 12 is attached to, or integrated into a dialysis component, which is shown in the present figure as the reusable module 11. The RFID tag 12 comprises a transponder 32 and RF antenna 31. The reader 33 may be disposed on a sorbent cartridge or other component of a dialysis system. Alternatively, the reader 33 may be a separate component wherein the user will cause the reader 33 to come close enough to the reusable module 11 to read the RFID tag 12. The reader 33 can have an RF source 34 and detector 35. The RFID tag 12 can be activated when an RF signal 37 is transmitted by the RG source 34 via an RF antenna 36. In response, the RFID tag 12 can transmit back a portion of the original RF signal 37 to the detector 35 via antenna 31 as signal 38. The transponder 32 can carry the identification and other data concerning the reusable module 11. This information, stored in the transponder 32, can determine which portions of the RF signal 37 to reflect back as signal 38. In one embodiment, a single antenna 36 can be used by both the source 34 and detector 35. In another embodiment, the source 34 and detector 35 can each have separate antennae.

The detector 35 is capable of detecting the RF signal reflected back by the RFID tag 12 and transmitting the information to a processor 39 via either wireless or wired communication. This information can be used to determine whether the reusable module 11 is certified, how often the module has been used, and any other information. The processor 39 can also determine if the dialysis component shown as the reusable module 11 is matched to the correct patient or dialysis prescription. The processor 39 can optionally comprise a memory device, such as a processor used in a computer. This allows the processor 39 keep track of the information received from the detector 35.

The processor 39 can optionally include a user interface 40 such as when the processor is being used in a computer. The user interface 40 will allow the user to interact with the processor 39. The user interface 40 may allow the user to see the identification and other information stored in the RFID component transponder 32. The user interface 40 may also allow the user to make changes to the information stored in the RFID component transponder 32. In embodiments where the processor 39 automatically disables use of the system in the event of non-certified parts being used or parts used beyond their useful lives, the user interface 40 may allow the user to override the processor 39.

The RFID component 12 may be affixed to the reusable module 11 by using an adhesive. The adhesive selected would ideally be an adhesive that will not significantly degrade with use or time. This will keep the RFID component 12 from falling off during use, shipping, or handling. Alternatively, the RFID component 12 may be embedded within the housing of reusable module 11. This will ensure that the RFID component 12 cannot fall off of reusable module 11 and will prevent tampering with the component. Other known methods for affixing the RFID tag known to those of ordinary skill are contemplated by the invention.

Figure 5:
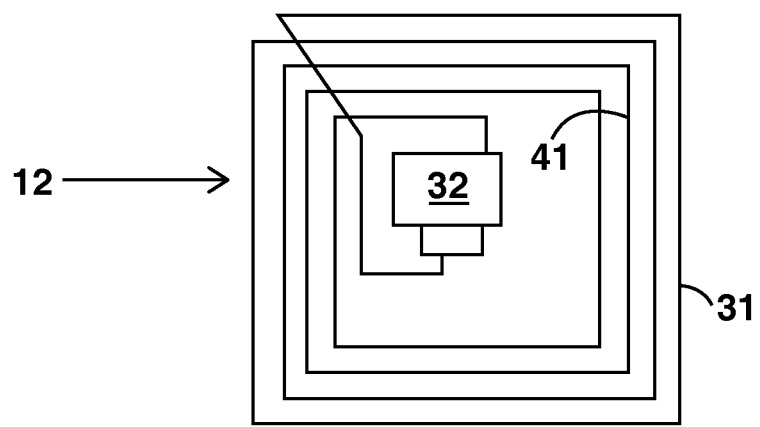
FIG. 5 shows a Tag-It™ RFID tag.

The RFID component 12 can be any known RFID tag or commercially available RFID tag. One non-limiting example is the TIRIS Tag-It™ smart label made by Texas Instruments. The Tag-It™ system is shown in FIG. 5. The Tag-It™ smart label provides for an ultra-thin form that can be laminated into a paper or plastic label. The RFID tag 12 includes the antenna 31 and transponder 32, which includes circuit 41. The circuit 41 comprises the memory and RF processor functions. Because the RFID component is ultra-thin and capable of being laminated into a paper or plastic label, the RFID component can be easily attached to the sorbent module 11 without the need for extra space. Other known labels known to those of ordinary of skill in the art are contemplated by the present invention. The type, manufacturer, or composition of the RFID tag is not critical to the present invention and any known alternative known to those of ordinary skill for the intended purpose is contemplated by the invention.

Figure 18:
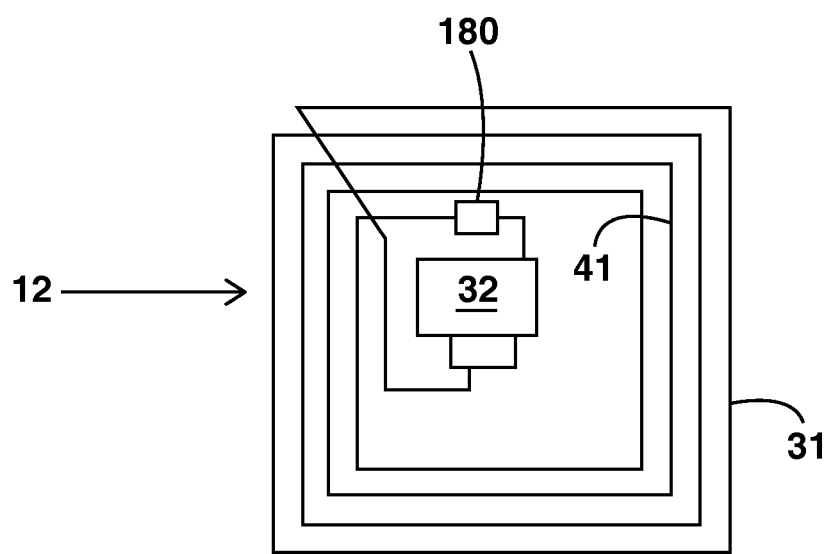
FIG. 18 shows an RFID component with a microchip for storing memory.

In some embodiments, the RFID component may also include a microchip 180 on the integrated circuit, as shown in FIG. 18. The microchip 180 can contain information about the history of the product, including manufacturer, date of manufacture, number of uses, and other information. The information on the microchip 180 can be sent to the reader. This embodiment can allow the memory to be fully integrated into the RFID tag, and therefore eliminate the need for an external processor to write to the RFID tag.

The RFID component 12 may be active or passive. In a passive device, the incoming RF signal 37 provides enough power for the RFID component 12 to operate. Such an embodiment eliminates the need for a power source coupled to RFID component 12. In an alternative embodiment, RFID component 12 may have its own power source (not shown) and operate as an active component. Such an embodiment may allow a more powerful return signal 38.

Figure 6:
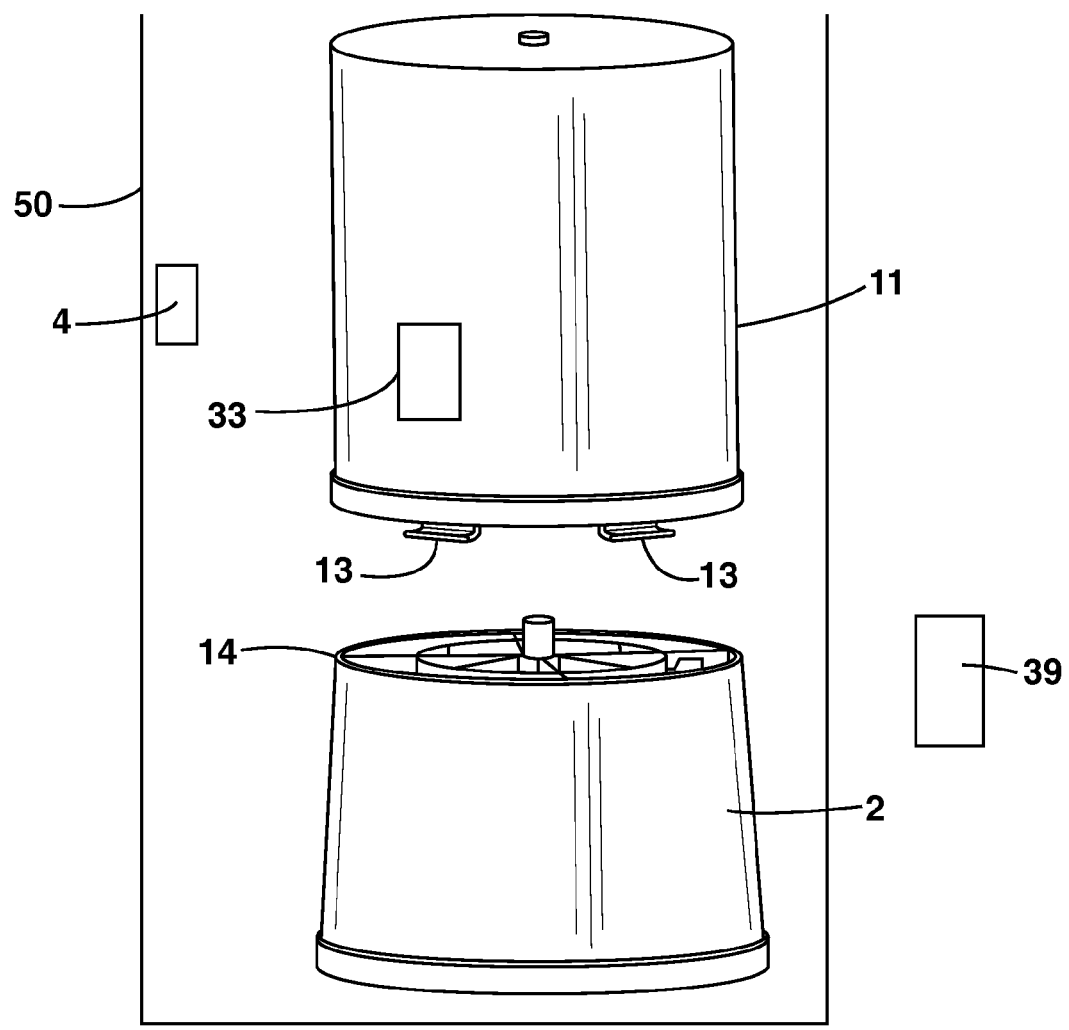
FIG. 6 shows a modular sorbent cartridge with modules utilizing an identification component.

One non-limiting embodiment of the invention is shown in FIG. 6. When the operator connects the detachable module 11 to the sorbent cartridge represented schematically as an open-ended rectangular box 50, or to the second module 2, the reader 33, housed internally within the sorbent cartridge 50, can automatically read the identification component 12. The detachable module 11 may connect to the second module 2 by mating the latches 13 with annular connection ring 14 by engaging the latches 13 with engagement members disposed on the annular connection ring 14. In other embodiments, the reader can be formed as part of a dialysis machine (not shown). If the detachable module(s) form the body of the sorbent cartridge, i.e., there is no casing or body and the modules form a unitary cassette, then the reader can be configured on any convenient location on the dialysis machine sufficient to provide for transmitting and receiving a signal. This information is transmitted to processor 39, which can be programmed to determine one or more features such as whether the detachable module 11 is matched to the particular sorbent cartridge, and to the particular patient, while at the same time tracking the usage of the detachable module 11. In an alternative embodiment, the reader 33 may not automatically read the identification component 12. Instead, the user may control when the reader 33 reads the identification component. If the detachable module 11 does not match the proper manufacturer-specific unique identifier, dialysis component-specific unique identifier and/or patient-specific unique identifier, the system may inform the user of this fact and/or disable usage. If the detachable module 11 is reusable, the system may inform the user whether the module has reached the end of its useful life and/or its remaining useful life. Because both of the modules may be reusable, in an alternate embodiment, both of the modules can have identification components.

Figure 7:
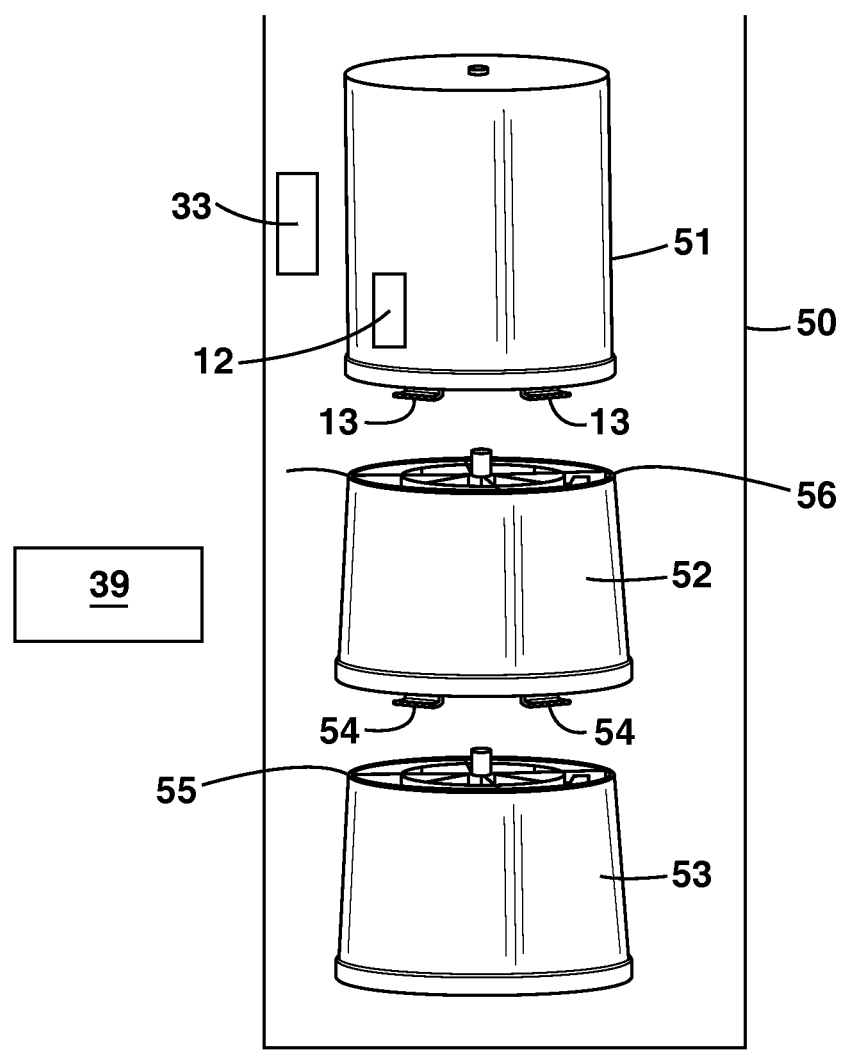
FIG. 7 shows a three module sorbent cartridge utilizing an identification component.

A modular sorbent cartridge may include more than two modules. FIG. 7 shows an authentication system for use with a modular sorbent cartridge involving three modules. Spent dialysate enters the sorbent cartridge represented schematically as an open ended rectangle 50 at the bottom and flows through sorbent module 53, through a connector to sorbent module 52, attached to the first sorbent module 53 by mating latches 54 with annular connection ring 55, and through a second connector to sorbent module 51, attached to sorbent module 52 by mating latches 13 annular connection ring 56. As before, it will be understood that modules 51, 52, and 53 can form a unitary body to form the sorbent cartridge to be connected to a dialysis machine wherein an outer casing of the sorbent cartridge represented by rectangle 50 is not present. In such case, the connected modules forming a unitary body can be considered the sorbent cartridge 50. An identification component 12 may be affixed to, or embedded in, reusable module 51. The reader 33 may be affixed to, or embedded in the sorbent cartridge 50. Alternatively, and as described herein, the reader can be formed as part of a dialysis machine (not shown). The reader 33 can automatically read the identification component 12. This information can be transmitted to processor 39, which can be programmed to determine one or more of whether the detachable module is matched to the particular sorbent cartridge, and to a particular patient, while at the same time tracking the usage of the detachable module. Alternatively, the user may cause the reader 33 to read the identification component 12 instead of the identification occurring automatically. In alternative embodiments, any one or more of the modules may have an identification component. The invention is not limited to sorbent cartridges having one, two, or three modules. Sorbent cartridges including any number of modules are contemplated. Any number of these modules may be reusable, and any number may have their own identification components.

Figure 8:
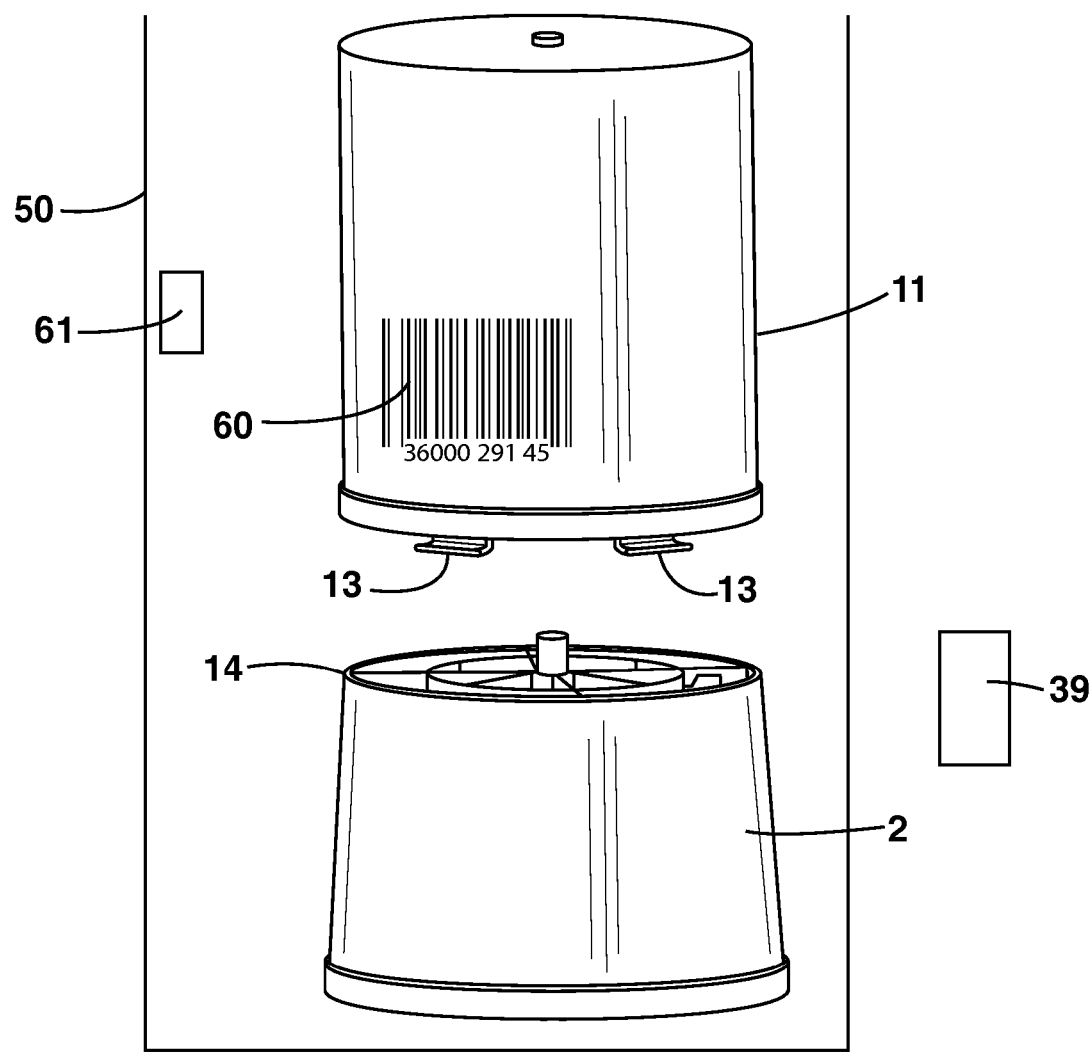
FIG. 8 shows a barcode as an identification component.

The invention is not limited to RFID components. The identification component may be any component capable of being used for identification purposes known to those skilled in the art. For example, FIG. 8 shows an embodiment wherein the identification component is a bar code instead of an RFID. Barcode 60 can be affixed to reusable module 11. The barcode 60 can be read by barcode reader 61. Barcode reader 61 may be permanently affixed to the sorbent cartridge 50, or the barcode reader 61 may be an external device. The reader 61 can transmit the information from the barcode 60 to a processor 39 through wired communication or wirelessly. The processor 39 can determine whether the reusable module 11 is a certified part, whether the reusable module 11 is matched to the correct sorbent cartridge and patient, and/or track the usage of the reusable module 11. As before, it will be understood that modules 11 and 2 can form a unitary body wherein an outer casing of the sorbent cartridge represented by rectangle 50 is not present. In such case, the connected modules forming a unitary body can be considered the sorbent cartridge and the barcode reader 61 may be an external device positioned on any part of a dialysis machine or flow path sufficient to provide for adequate communication with the barcode 60.

Figure 9:
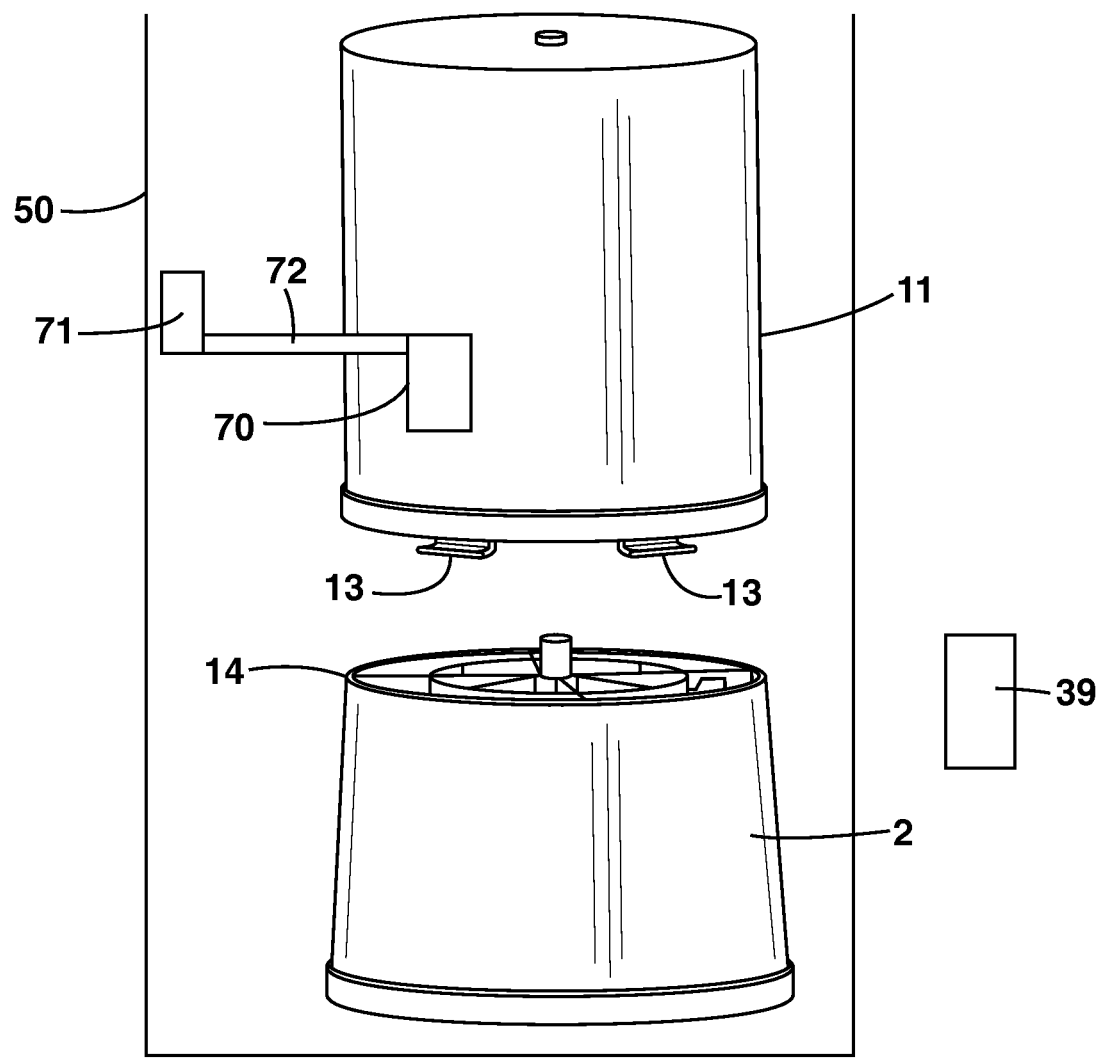
FIG. 9 shows a one-wire security component as an identification component.

FIG. 9 shows an embodiment utilizing a one wire security component as an identification component. A one wire security component comprises two portions, an identification portion 70 and a reader portion 71. The identification portion 70 can be affixed to the reusable module 11. The reader portion 71 can be affixed to the sorbent cartridge 50. When the reusable module 11 is placed into or forms the sorbent cartridge 50, a connection can be formed across wire 72. The "wired connection" can also be an electrical contact between one or more surfaces of any kind and not require a physical wire to be considered a one wire security component. For example, a first electrically conducting plate contacting a second electrically conducting plate can be considered a "one wire" component. The identification component 70 can send an electrical signal to the reader component 71, across the wire 72. This signal can contain the identification and other information. The reader component 71 can then relay this information to processor 39 to determine whether the reusable module 11 is certified, whether the reusable module has exceeded its useful life, tack usage of the reusable module and/or whether the reusable module is matched to the correct patient.

Figure 23:
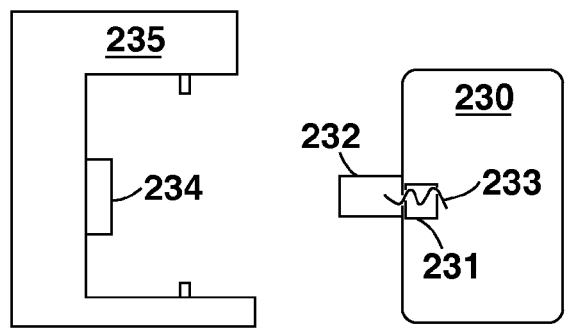
FIG. 23 shows an authentication component requiring electrical contact with the reader.

FIG. 23 shows a direct electronic connection identification component. These components require a direct connection between the identification component and reader to operate. The identification component 231 can be affixed to dialysis component 230. The identification component can be covered by a conductive flap 232, held in an open position by spring 233. The reader 234 can be placed on the dialysis machine 235. The reader 234 should be positioned so that when the dialysis component 230 is connected to complete the flow path, the flap 232 is pushed closed, compressing spring 233 and contacting identification component 231. This completes the circuit between the identification component 231 and reader 234, allowing information to be transmitted from the identification component 231 to reader 234.

Figure 10:
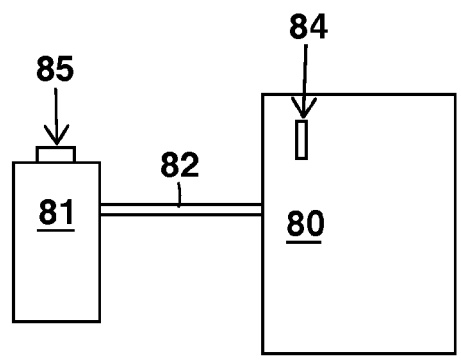
FIG. 10 shows a recharger utilizing an identification component.

Recharging of the sorbent material within a reusable module of a sorbent cartridge can be performed without sending the reusable module out to be recharged as described in FIG. 3. Instead, rechargers may be attached to the sorbent cartridge to recharge the reusable modules in-line as shown in FIG. 10. Before the recharging starts, the recharger 80 can be attached to the sorbent module to be recharged 81 by tubing 82. The reader 85 can automatically read the identification component 84, which can be affixed to the recharger 80, and ensure that the recharger is correct for the particular sorbent module. When the reader 85 correctly identifies the recharger 80, the information can be sent to a processor 83 with a memory component. The memory component can track the recharging, and ensure that a sorbent module 81 is correctly recharged before being reused. This can keep the wrong recharging fluids from entering the sorbent module 81, which will ensure proper recharging and avoid damaging the sorbent materials by using an incorrect recharging method. By utilizing a manufacturer-specific unique identifier, the system also ensures that counterfeit sorbent modules or rechargers cannot be used. The identification component 84 may be affixed to the outside of the recharger 80 as described above, or the identification component 84 may be embedded within the housing of the recharger 80. Alternatively, the reader 85 may be affixed on or embedded into part of the recharger 80, and the identification component 84 may be affixed on or embedded into the sorbent module 81.

Figure 11:
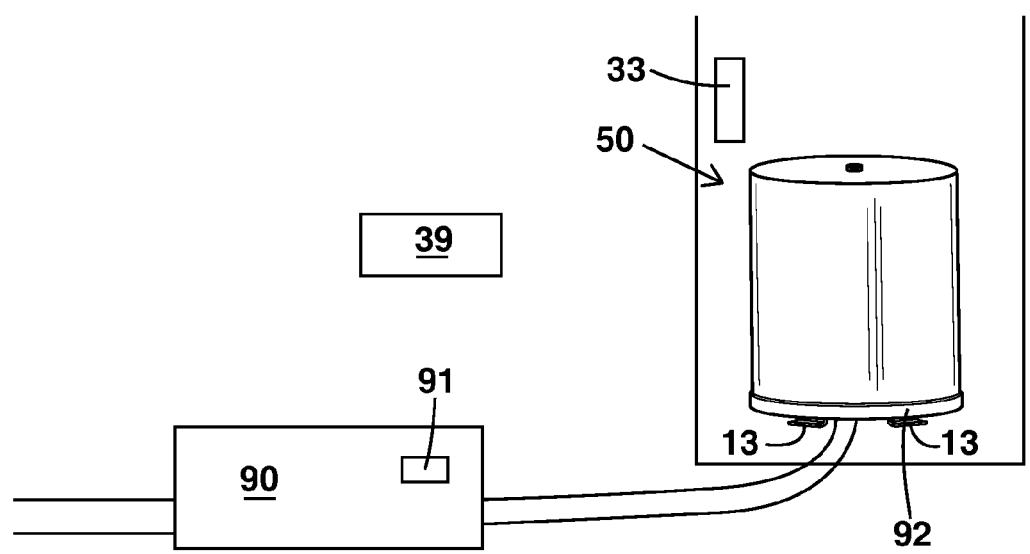
FIG. 11 shows a dialyzer utilizing an identification component.

In an alternative embodiment shown in FIG. 11, the identification component may be utilized with a dialyzer. Identification component 91 may be affixed to or embedded in dialyzer 90. The sorbent cartridge 50, containing module 92, can have a reader 33 to read the identification component 91. The reader 33 can transmit the information from the identification component 91 to a processor 39. The processor 39 can determine if the dialyzer 90 is certified, and/or if the dialyzer 90 is being used for the correct patient. In an alternative embodiment, the sorbent cartridge 50 may have the identification component 91, and the dialyzer 90 may have the reader 33.

Figure 22:
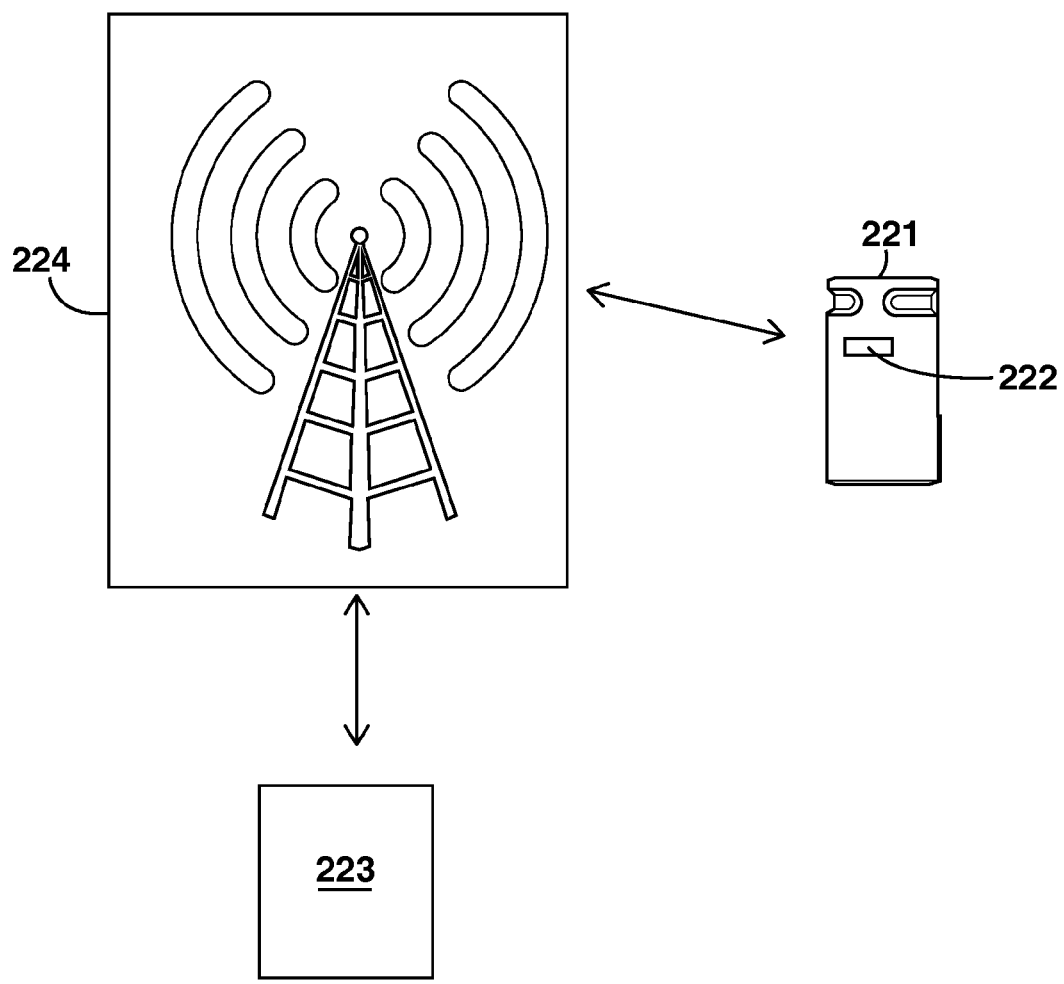
FIG. 22 shows a method for tracking the locations of dialysis components.

Tracking the physical locations of the dialysis components of a dialysis system is also contemplated by this invention. It is possible to utilize cellular networks in order to precisely locate an RFID tag that may be affixed on, or embedded in, the dialysis component, as shown in FIG. 22. The user 223 may send a request to a mobile host 224 to track a particular RFID tag 222 on dialysis component 221. In response, the mobile host 224 can then track the RFID tag. When the mobile host 224 detects the RFID 222 within its network, the host 224 can obtain the location of the tag 222. This information can be stored, along with a time stamp. The information can then be obtained by the user 223. This system enables tracking of the dialysis components even in locations that only have cellular networks, enabling tracking of the distribution of the modules in these areas. In alternative embodiments, the modules can be tracked using any other wireless technology. Non-limiting examples of possible wireless technology include bluetooth, WiFi, LTE, WiMax or any other wireless technology known to those of ordinary skill including proprietary wireless technologies.

The RFID can utilize a component-specific unique identifier such as a dialysis component-specific unique identifier or a module-specific unique identifier, or any of manufacturer-specific, patient-specific, and/or machine-specific unique identifiers. The manufacturer-specific unique identifier allows the processor to determine if the component is a counterfeit part. If so, the processor may disable use of the system, or alert the user of the non-certified part. The patient unique identifier can be utilized to ensure that specific components are only used by the specific patients for which they are intended. This can eliminate cross-usage by patients and contamination. The machine unique identifier can be utilized to ensure that specific components are being used together. For example, a recharger being used to recharge a sorbent module containing the correct sorbent materials.

Figure 20:
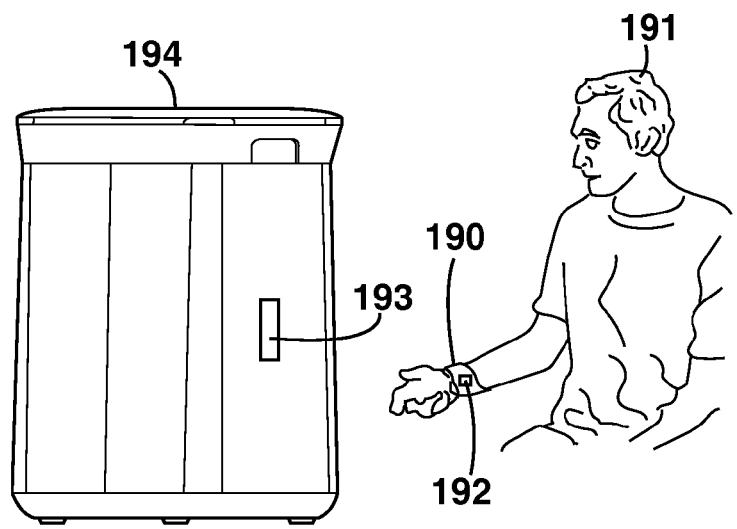
FIG. 20 shows a patient with an identification component and a reader on a dialysis cabinet.

To avoid the possibility of a user incorrectly entering or reading a patient-specific unique identifier, the patient may be given an article containing an identification component that can identify the specific patient. In FIG. 20, the article is shown as a wristband 190 on patient 191 with RFID tag 192. Before dialysis begins, the patient 191 brings the RFID tag 192 on the wristband 190 close enough to the reader 193 to be read. The reader 193 may be the same reader as is used for the dialysis components, or may be a different reader. For instance, the reader 193 may be, as shown, on the dialysis cabinet 194. In other embodiments, the article may be an identification card for the patient to carry, or any other article that can be made with an identification component. The information from the patient's identification component 192 can be transmitted to the processor, and in this way the user can be assured that the correct components are being used for the specific patient. The patient's RFID 192 can contain other information besides simple identification. For example, the RFID 192 can contain information regarding the patient's prescription, the date of the patient's last treatment, or any other information pertaining to the individual. Alternatively, the patient's RFID 192 may only contain identification information. In such an embodiment, the identification can be read by a processor containing a memory component. The memory in the processor can be updated to contain information such as the dates of the patient's dialysis sessions and the patient's prescription.

Figure 12:
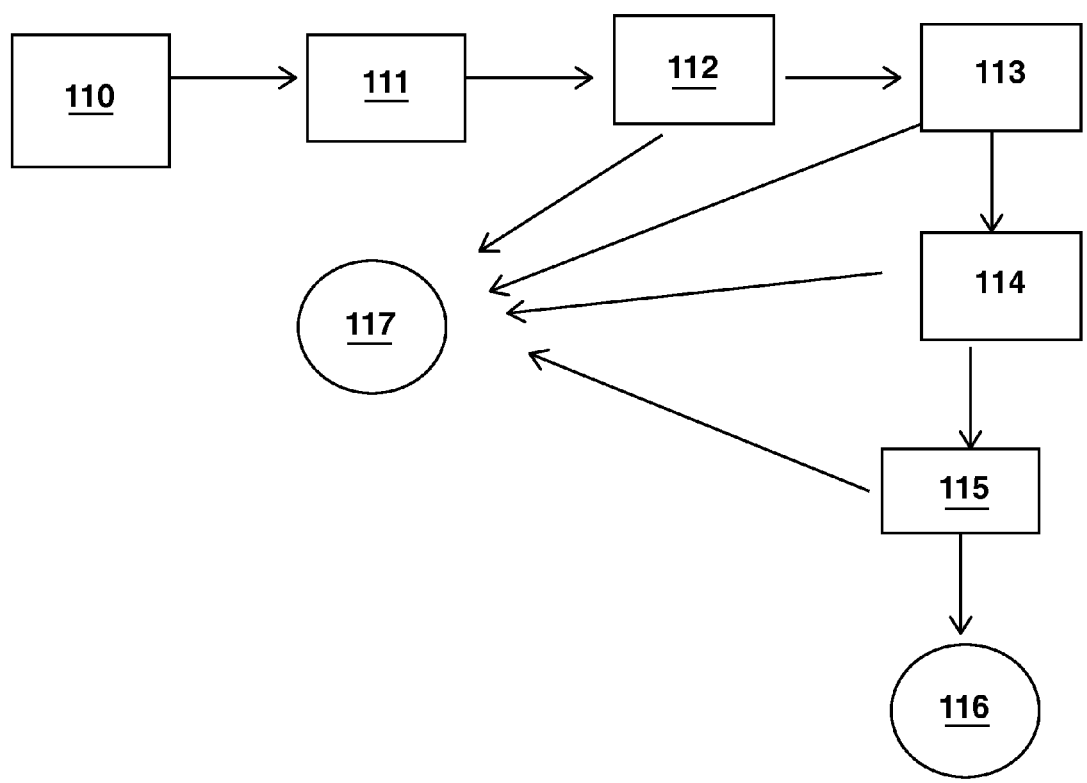
FIG. 12 is a flow chart showing the processing of information from the identification component.

Use of unique identifiers within the RFID or other identification component allows the user to be sure that the correct component is being used. An example is shown in FIG. 12. A reader can read the identification component in step 110 and transmit the information to a processor in step 111. If the component utilizes a manufacturer-specific unique identifier, the processor can determine whether the component is a manufacturer certified component in step 112. If not, the processor can warn the user and/or disable use of the dialysis system in step 117. If the manufacturer-specific unique identifier is correct, the processor will continue. If a patient-specific unique identifier is utilized, the processor can determine whether the component is correctly matched to the patient in step 113. If not, the processor can warn the user and/or disable use in step 117. If the patient-specific unique identifier is correct, the processor will continue. If a machine-specific unique identifier is utilized, the processor can determine if the component is being used in the correct machine in step 114. If not, the processor can warn the user and/or disable use in step 117. The processor can also store information each time the component is used, and thereby track usage in step 115. If the component's use is beyond its useful life, if the component has not properly been recharged prior to reuse, or if too much time has elapsed between uses of the component, the processor can warn the user and/or disable use in step 117. If the component has not been used to the end of its useful life, then the processor will allow its use in step 116. The processor can further monitor the contents of a sorbent cartridge such as Zirconium Phosphate (ZrP) using techniques for measuring ZrP levels inside the cartridge known to those of ordinary skill in the art. Based on the monitoring of the contents of the sorbent cartridge, the processor can provide an alert when the component is nearing or has reached the end of its useful life or requires recharging. In an alternative embodiment, the identification component may include a microchip for storing memory. In this embodiment, information about the number of times a reusable component has been recharged, or whether the reusable component is reaching the end of the component's useful life can be stored on the identification component itself.

The processor may determine the status report or answers to any inquiries outlined herein in any order. For example, the processor may first determine if the component has reached the end of its useful life, then whether the component is a certified component, then whether the component is matched to the correct patient, and then whether the component is matched to the correct machine. Any order of the above inquiries is within the scope of this invention. Further, even if the processor determines that the component fails at one of the inquiries, the processor can still determine the answer to the others. For example, if the processor determines that the component is matched to an incorrect patient, the processor may still determine whether the component is matched to the correct machine or whether the component has been used beyond the component's useful life. The information from any one or more of the inquiries may be displayed to the user by user interface 40 as described above.

It is contemplated that not all of the functions shown in FIG. 12 need to be performed for each component. More than one patient may use the same dialysis machine, recharger or other component. In such cases, the identification component may not include a patient-specific unique identifier. Alternatively, some components may not have their usage tracked, such as components that have no set end of useful life. The present invention covers any combination of these functions. In an alternative embodiment, the processor may transmit usage information to a wireless network, which will enable tracking of the usage of a component, even if different processors are used for the component at different times, or in different locations.

In embodiments where an RFID tag is the identification component, the tag may be a read-only tag, or a read/write tag. A read-only tag does not allow for altering of the information stored in the RFID tag. The information is loaded by the manufacturer, and cannot be changed. A read/write tag allows information stored by the RFID tag to be altered. This allows the user to encode certain information in the RFID tag. A read/write tag can also automatically alter information stored in the RFID tag, for example each time a sorbent module is placed within a sorbent cartridge.

Figure 13:
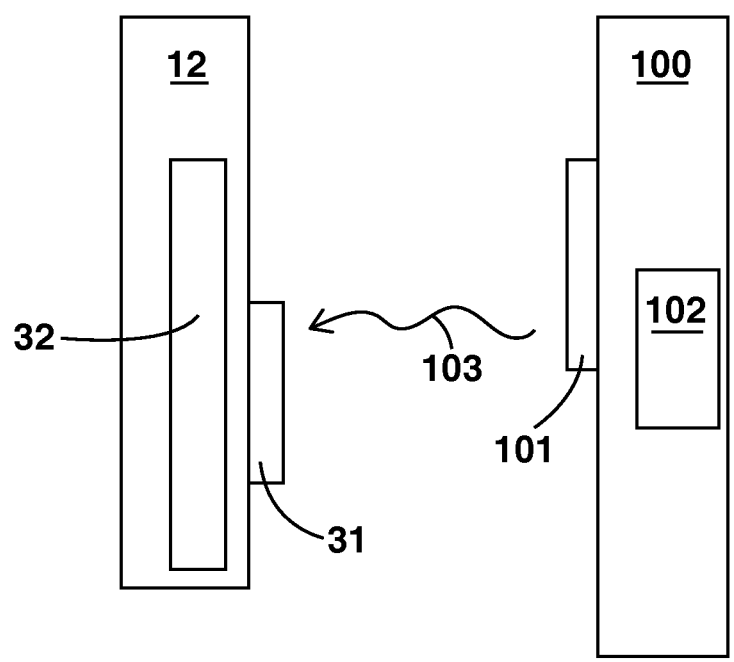
FIG. 13 shows a writer for writing to a writable RFID tag.

In addition to reading the identification component, the dialysis system may also contain a writer to write to a read/write identification component, as shown in FIG. 13. The RFID component 12 includes transponder 32 and antenna 31. The RFID writer 100 comprises a source 102 and antenna 101. When the writer 100 receives an input telling the writer 100 to write to the component 12, the source 102 generates an RFID signal that is transmitted by antenna 101. The signal 103 is received by the antenna 31 on the RFID tag 12, and the signal is transmitted to the transponder 32. In response to the signal 103, the transponder 32 will change specific information stored within the transponder circuitry (not shown). This information will then be included the next time the RFID tag 12 is read. This allows the identification component 12 to keep track of how many times the module has been used, and how long the detachable component has been in use. This will allow the user to disable or dispose of the reusable module prior to the module becoming overused, and thus avoid degradation of the therapy. In an alternative embodiment, a microchip may be placed on the transponder circuitry. The microchip allows for larger amounts of information to be stored and transmitted to the reader.

Figure 14:
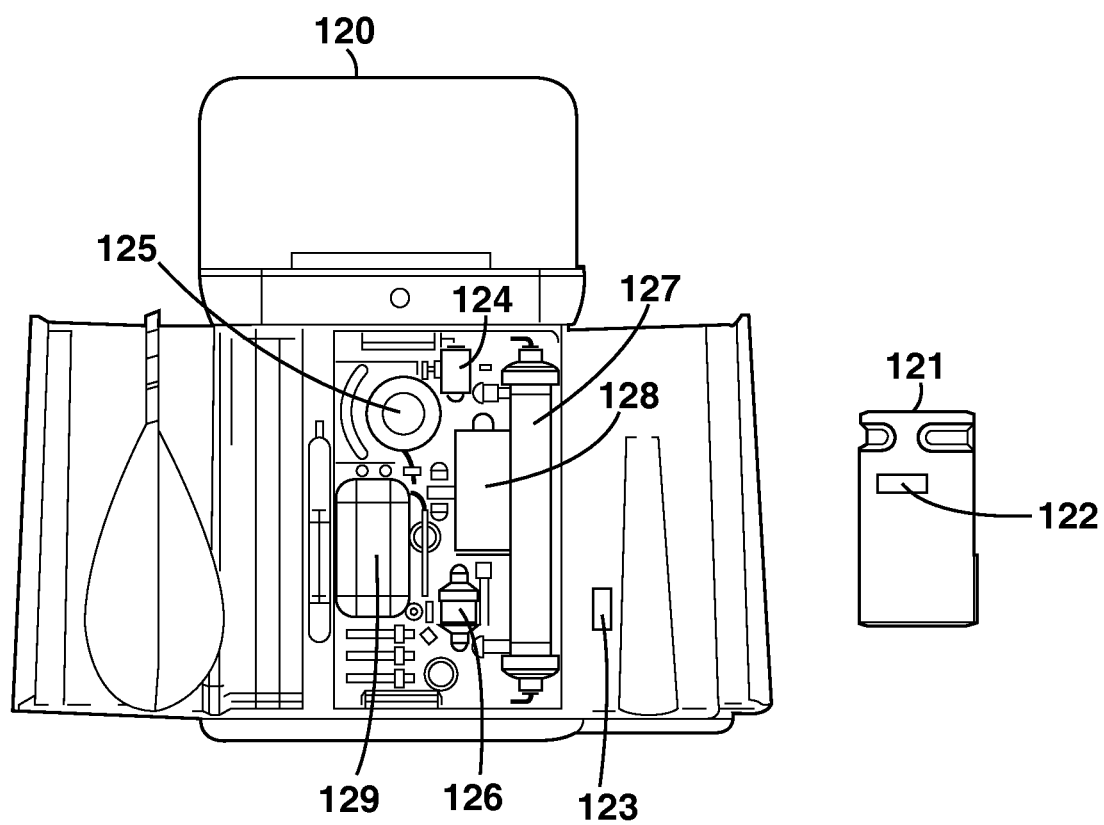
FIG. 14 shows an RFID tag on a detachable module in a dialysis cabinet.

FIG. 14 shows one, non-limiting, embodiment of the invention in use. The RFID tag 122 is affixed to, or embedded within, sorbent cartridge 121. RF reader 123 is affixed to or embedded in, the housing of the sorbent cabinet 120. FIG. 14 shows the reusable sorbent cartridge 121 outside of the dialysis cabinet 120. When the sorbent cartridge 121 is placed inside the cabinet 120 for use, the reader 123 will read the information from the RFID tag 122, and send the information to a processor (not shown). If the sorbent cartridge 121 is not a certified part, not matched to a correct machine or patient, or has been used beyond the cartridge's useful life, the processor may notify the user and/or disable use of the system. The reader 123 may be at any location in or on the cabinet 120, but is ideally within the range of the RFID tag 122. In an alternative embodiment, the reader 123 may not be in range of RFID tag 122 while in use, but the user may bring the reusable cartridge 121 within range of reader 123 before inserting the reusable cartridge 121 into the dialysis cabinet 120. The dialysis cabinet 120 also includes a dialyzer 127, a degasser 124, a motor 123, a bicarbonate reservoir 128, a cation reservoir 129, and a NaCl cartridge 126. Any one or more of these components may be reusable. In alternative embodiments, any one or more of these components may have an RFID tag.

Figure 19:
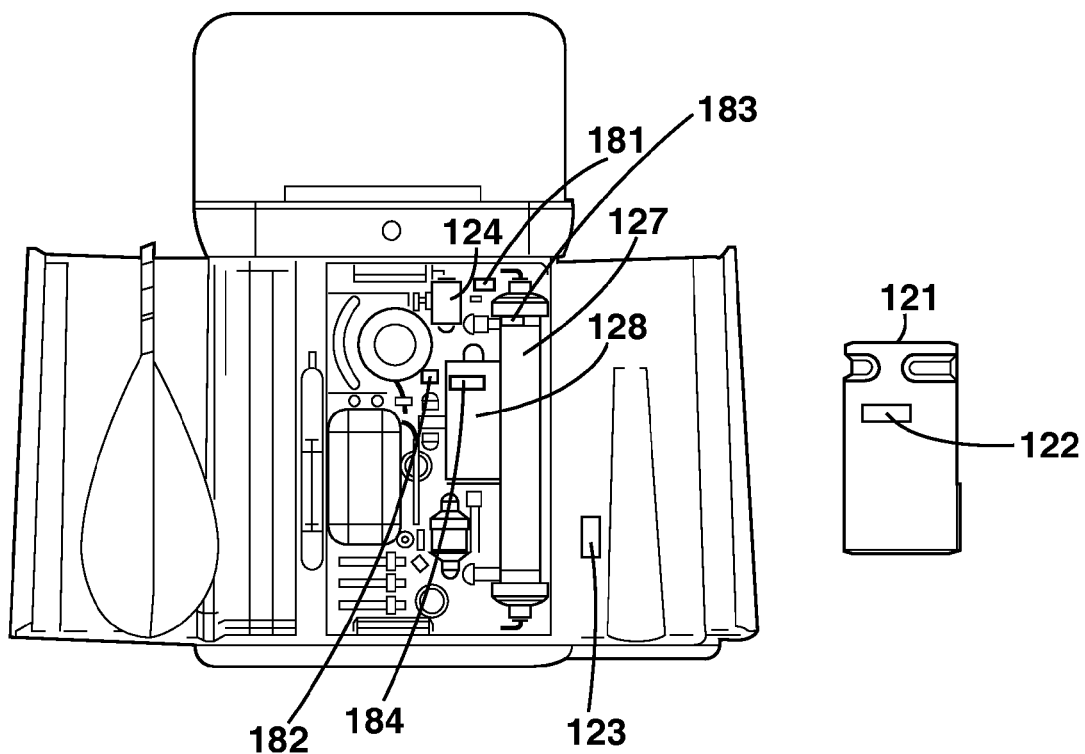
FIG. 19 shows a dialysis cabinet where multiple components have authentication components and the dialysis cabinet has multiple readers.

Given that RFID tags have a limited range, in embodiments where more than one component has an RFID tag, more than one RFID reader can be included. For example, in FIG. 19, sorbent cartridge 121 has RFID tag 122; dialyzer 127 has RFID tag 183; and reservoir 128 has RFID tag 184. Because the RFID tag on dialyzer 127 may not have enough range to communicate with reader 123, a second reader 181 can serve as the dialyzer RFID reader. Similarly, reader 123 can serve as the sorbent cartridge reader, and reader 182 can serve as the reservoir reader. In alternative embodiments, any number of readers can be utilized, depending on the number and locations of components with RFID tags affixed.

Figure 15A:
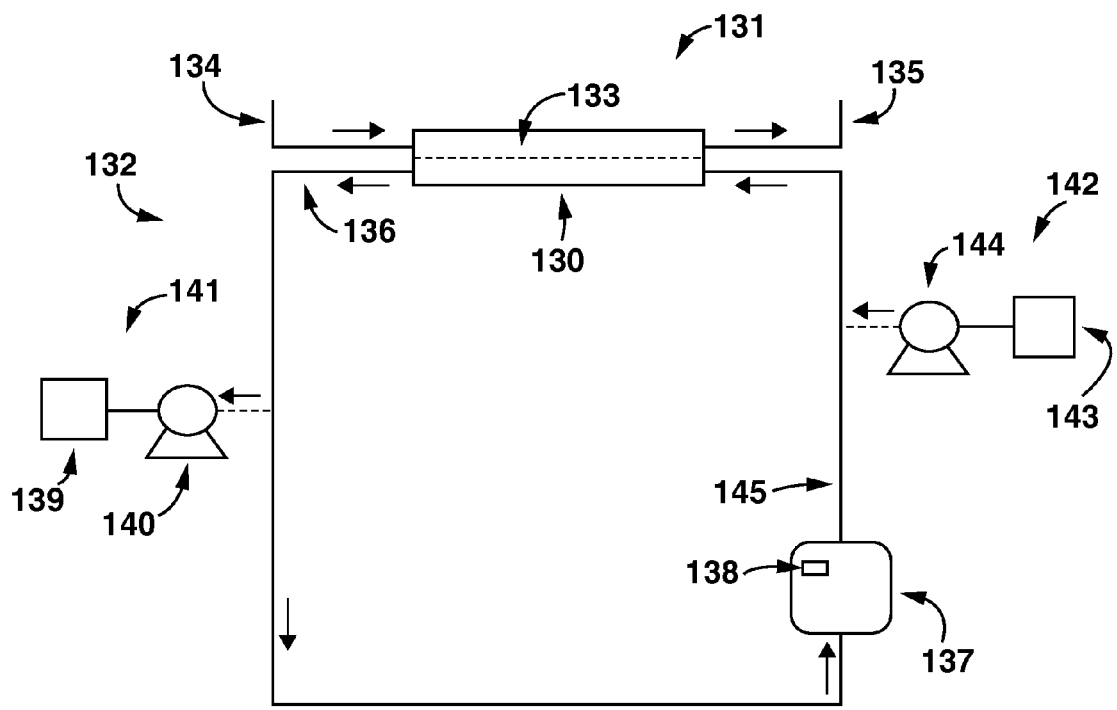
FIGS. 15a and 15b show a detachable module with an RFID tag in a dialysis circuit.
Figure 15B:
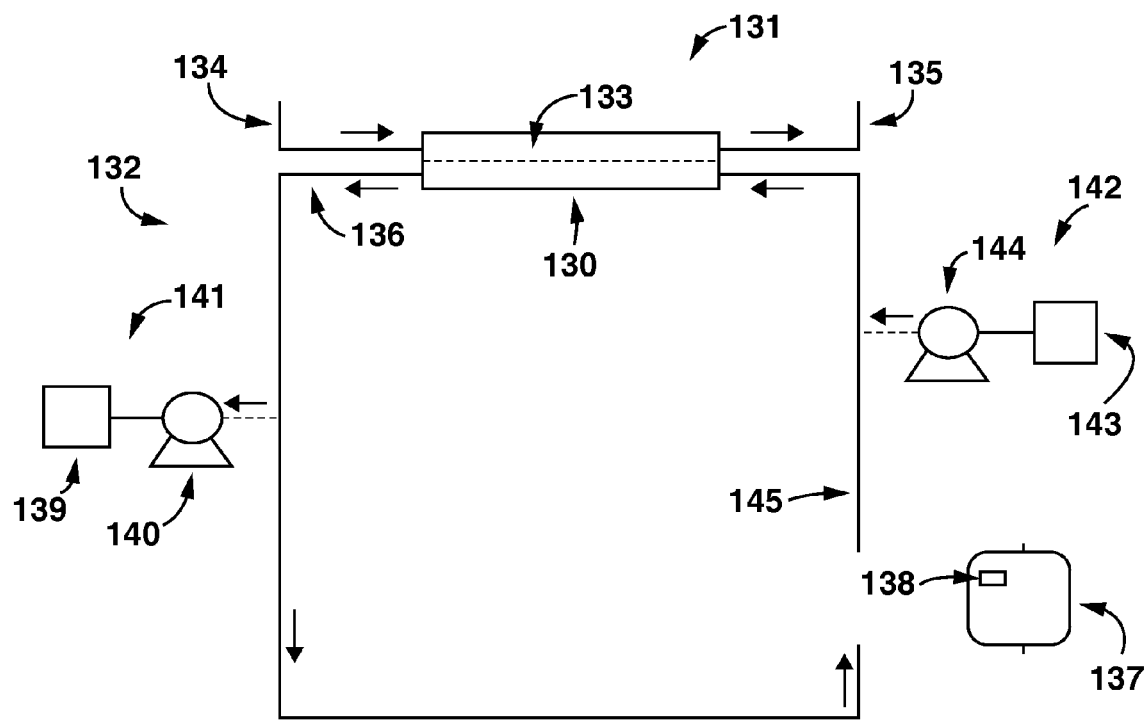

FIGS. 15*a* and 15*b* show a reusable sorbent cartridge in use in a dialysis circuit. The sorbent dialysis circuit includes a blood circuit or flow path 131, and a dialysate regeneration circuit or flow path 132, separated by a membrane 133 of the dialyzer 130. The blood enters the dialyzer 130 through a blood line inlet 134 and exits through a blood line outlet 135. The dialysate flow loop 132 is a controlled compliant flow loop. The blood flowing through the dialyzer 130 via flow path 131 can exchange waste compounds across the membrane 133 with the dialysate flowing through the dialyzer 130 via flow path 132.

The dialysate that has gone through the dialyzer 130 exits as spent dialysate 136. The spent dialysate may pass an ultrafiltration system 141, which can include an ultrafiltration pump 140 and ultrafiltration reservoir 139. The ultrafiltration pump 140 can remove fluid from the dialysate flow path 132, which draws fluid across the membrane 133 from the blood. The fluid removed by the ultrafiltrate pump 140 is collected in ultrafiltrate reservoir 139.

Regeneration of dialysate in the dialysate regeneration flow path 132 occurs at the reusable sorbent cartridge 137. The sorbent cartridge 137 contains sorbent materials that can remove specific toxins from the dialysate, or break down toxins into non-toxic compounds.

After exiting the sorbent cartridge 137 the clean dialysate may lack certain ions, such as potassium, calcium, or magnesium that need to be added before re-entering the dialyzer 130. This can be accomplished by the infusate system 142. The infusate system 142 can comprise infusate pump 144 and infusate reservoir 143. The infusate reservoir 143 may contain a concentrated solution containing the specific ions that need to be added to the dialysate before crossing into the dialyzer 130. After passing through the infusate system 142, the dialysate is fully regenerated and can pass back through the dialyzer 130.

The sorbent cartridge 137 may be reusable. In order to ensure that the cartridge 137 is a certified component, correctly matched to the correct machines, and still within the cartridge's useful life, an identification component 138 may be attached to the cartridge 137, or embedded within the cartridge 137.

When dialysis is complete, the reusable sorbent cartridge 137 may be removed from the dialysis circuit as shown in FIG. 15b. This can be performed to replace the cartridge 137, or to recharge the sorbent materials within. After the sorbent cartridge 137 is placed back into the circuit as shown in FIG. 15a, a reader (not shown) can read the identification component 138 to make sure that the correct cartridge is being used. The identification component may additionally, or alternatively, be affixed to any of the components of the dialysis system described.

Figure 16:
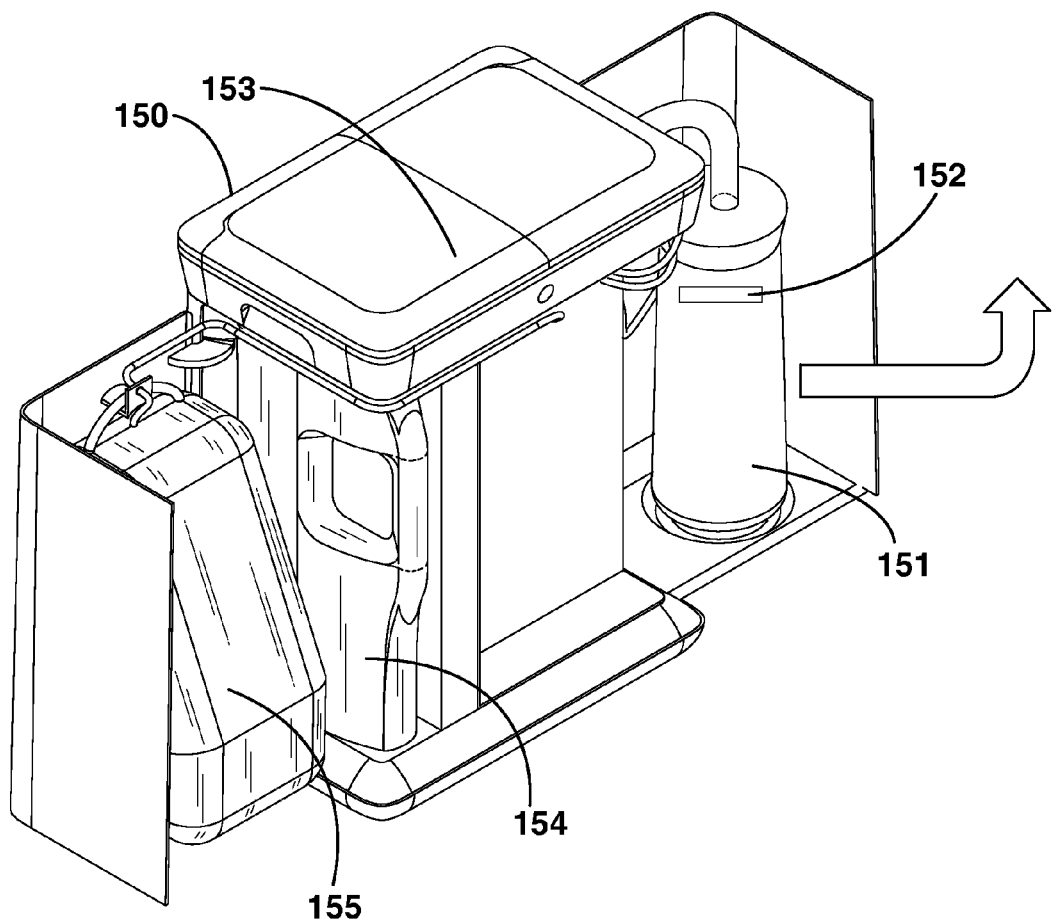
FIG. 16 shows a dialysis cabinet with a detachable sorbent cartridge having an RFID tag.

FIG. 16 shows an embodiment of the invention wherein the authentication component 152 is on the sorbent cartridge 151. In use, sorbent cartridge 151 is attached into the dialysis cabinet 150. The cabinet also includes attachments for water supply 154 and an ultrafiltrate reservoir 155. The water supply 154 is used to generate the initial dialysate and for use with the infusate systems (not shown). Ultrafiltrate removed from the patient is directed into the ultrafiltrate reservoir 155. The cabinet also includes a console 153. The console 153, when opened, provides an interface for the user. In some embodiments, the console 153 will display whether or not the RFID 152 matches the particular manufacturer, machine and/or patient, and any other information received from the RFID, such as an expiration date or number of times the component has been used. In an alternative embodiment, the RFID 152 can contain only identification information, and console 153 can contain a database that updates all other information in response to the identification received from the RFID 152. Additionally, the console 152 may communicate with an external database that contains this information.

Figure 17A:
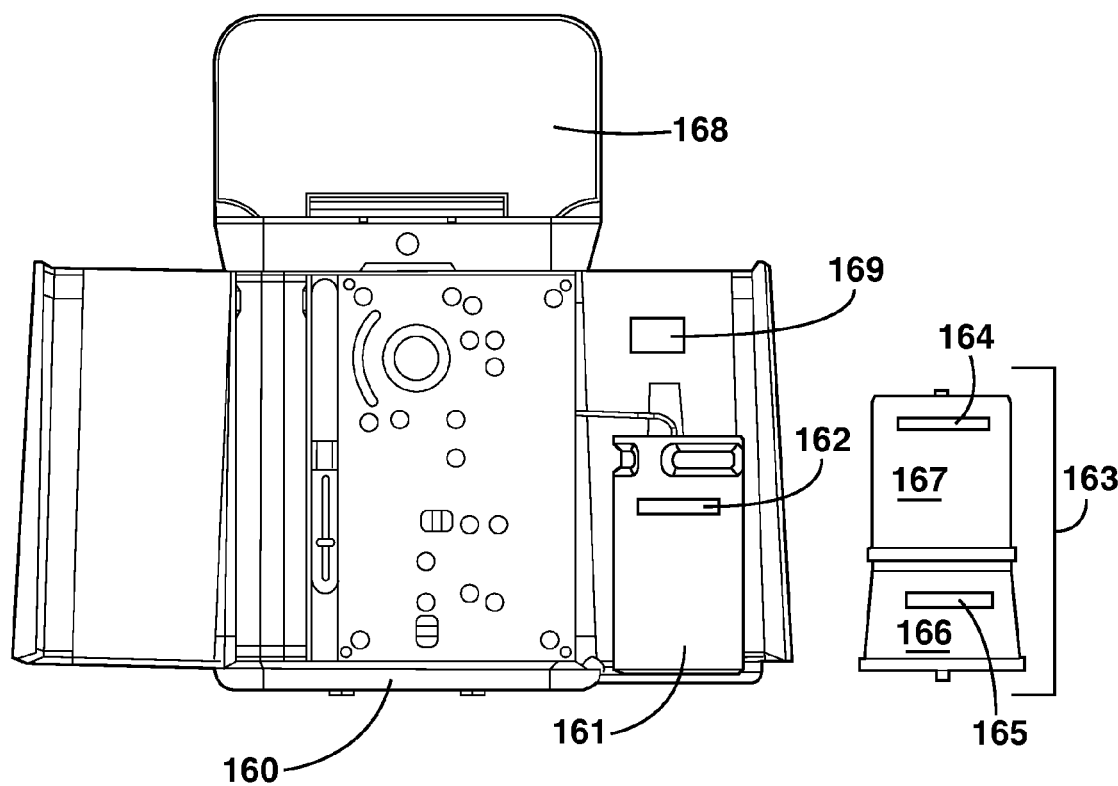
FIG. 17a shows a dialysis cabinet with a detachable sorbent cartridge that comprises two detachable modules.

FIG. 17a shows a different embodiment of the invention. Sorbent cartridge 161 can contain two modules. The first module 166 and the second module 165 can be connected to provide the two module system 163. The two module system 163 can fit within the casing to form a sorbent cartridge 161 for use in a dialysis system. Alternatively, the two module system 163 can be defined as the sorbent cartridge where a casing such as shown by the sorbent cartridge 161 is not used. Sorbent cartridge 161, first module 166, and second module 167 can all have authentication components affixed on them, or embedded within them. Authentication component 162 is shown on sorbent cartridge 161, authentication component 165 is shown on first module 166, and authentication component 164 is shown on second module 167. The dialysis cabinet 160 may include a reader 169, which can read each of the authentication components. If any of the authentication components do not match the manufacturer-specific, user-specific, or machine-specific unique identifiers, or if any of the components have reached the end of their useful lives, or have not been properly recharged, the user may be notified by console 168.

In other embodiments, the sorbent cartridge 161 may have a reader (not shown), as described above. This reader can notify the user if either of the modules 166 and 167 do not match the manufacturer-specific, user-specific, or machine-specific unique identifiers, or if either of the modules 166 and 167 have reached the end of their useful lives. Notably, the reader is not required in embodiments where the two module system 163 is defined as the sorbent cartridge where a casing such as shown by the sorbent cartridge 161 is not used In other embodiments, more than two modules can be used as described above. Sorbent cartridges with three, four, or more modules are contemplated. The two or more modules may fit into a casing or not. Each of the modules may be detachable and/or reusable, and each may be fitted with an authentication component.

Figure 17B:
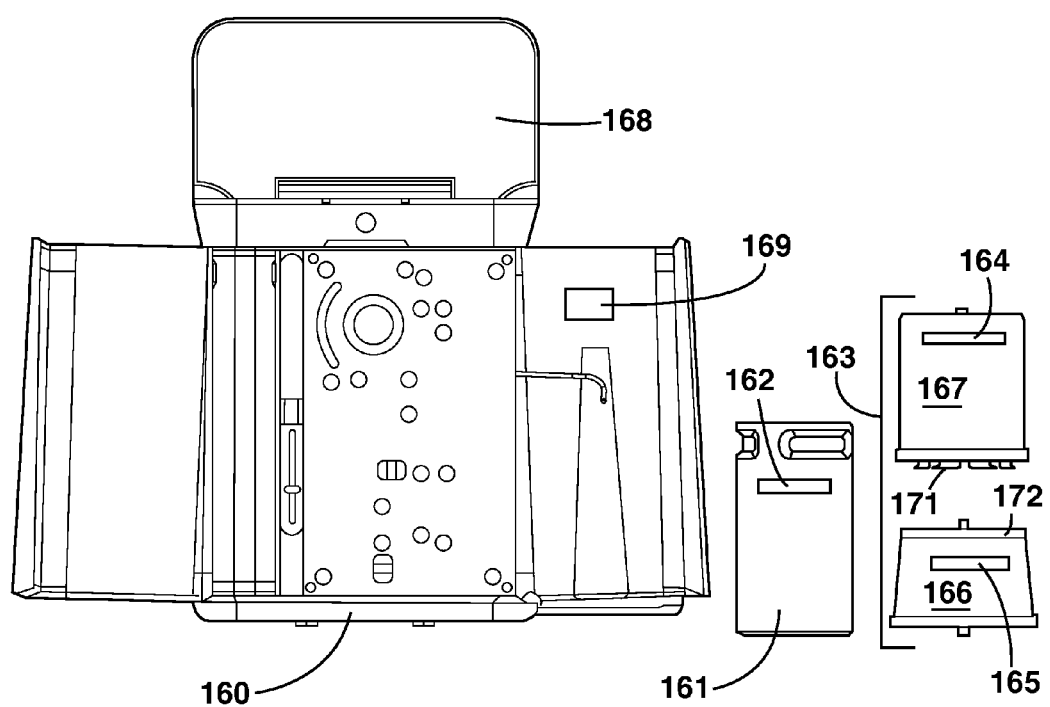
FIG. 17b shows a dialysis cabinet with the sorbent cartridge removed and the modules detached.

Each of the components may be detachable from the dialysis cabinet 160 as shown in FIG. 17b. As explained above, the individual modules 166 and 167 may be disconnected from one another by disengaging latches 171 from the engagement members on annular connection ring 172 so as to separately recharge, recycle, or dispose of the modules. By supplying first module 166 with authentication component 165, second module 167 with authentication component 164, and sorbent cartridge 161 with authentication component 162, the user can be assured that each component is certified, matched to the correct user and machine, and that each component is still within that component's useful life.

Figure 17C:
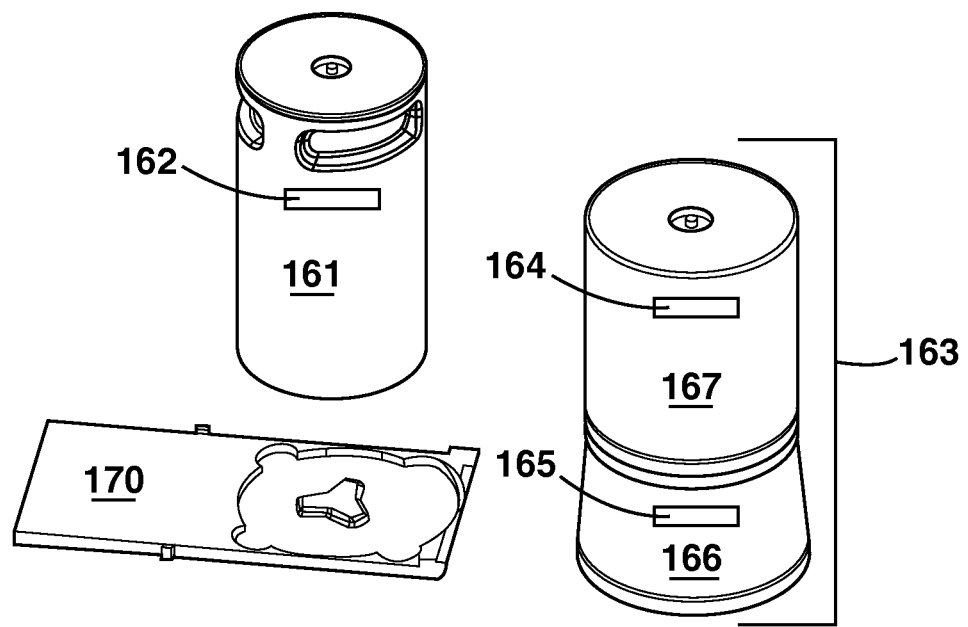
FIG. 17c shows the assembly of a detachable sorbent cartridge.

The assembly of the various components is shown in FIG. 17c. First module 166 with authentication component 165 can be connected to second module 167 with authentication component 164 to make the two-module system 163. The two module construct 163 can slide into the sorbent cartridge 161, which may be fitted with authentication component 162 and/or a reader (not shown). The sorbent cartridge 161 can attach to connector 170, which can be attached to the dialysis cabinet 160 for use in sorbent dialysis.

Figure 21:
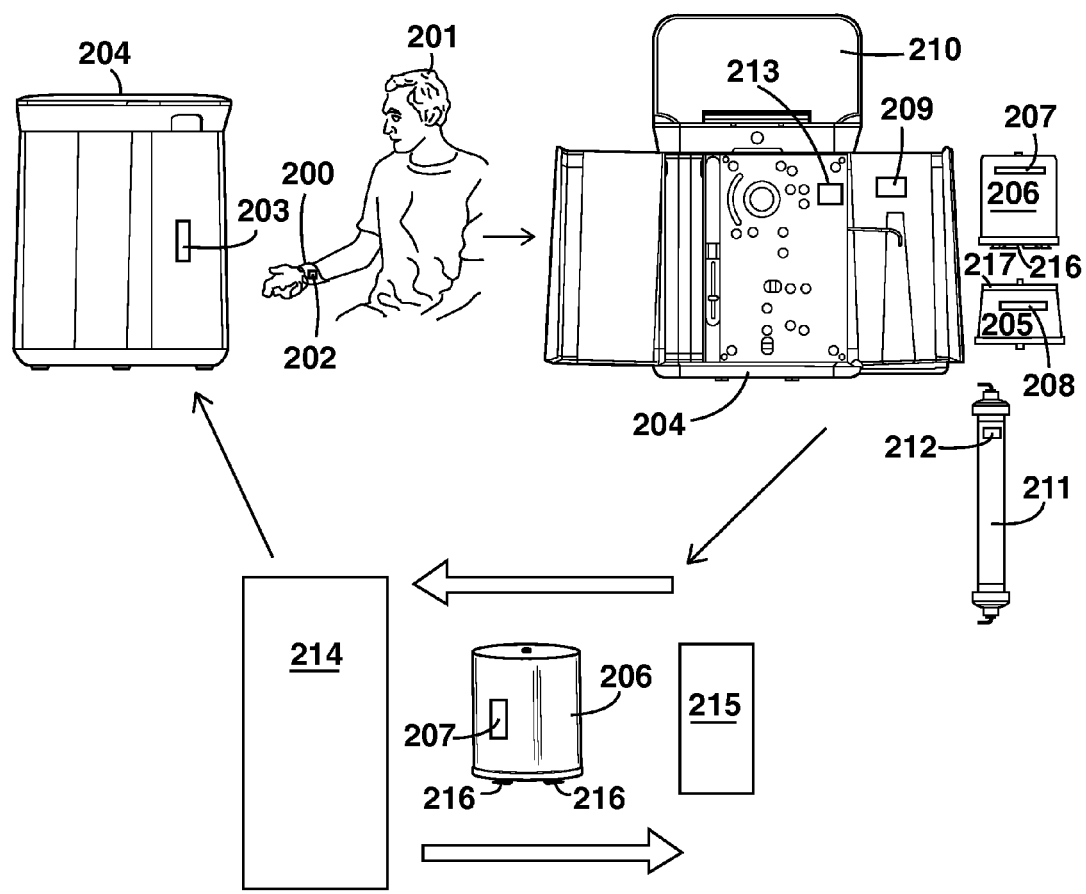
FIG. 21 shows a method for identifying and tracking multiple dialysis components.

FIG. 21 shows one embodiment of the identification/authentication system. When patient 201 is ready to begin dialysis, a RFID reader 203 on the dialysis cabinet 204 can read the patient's RFID tag 202 on wristband 200. In addition to the patient ID, the RFID 202 can contain information about the patient's prescription or their last session. In certain embodiments, this information can be transmitted to the patient of a clinician (not shown). After identifying the patient 201, the system can read the RFID tag 208 on a non-reusable module 205 using a first RFID reader 209. Ideally, this reader will be close enough to the position of the non-reusable module 205 that the reader automatically reads the RFID tag 208 when the non-reusable module 205 is placed in the dialysis cabinet 204. The system can confirm that the non-reusable module 205 is a certified component, that the non-reusable module 205 has not been used, and that the non-reusable module 205 is within its expiration date. The system can then read the RFID tag 207 on reusable sorbent module 206. Again, the reader 209 will ideally be close enough to the reusable module 206 to automatically read the RFID tag 207. The system can confirm that the reusable module 206 matches the patient identification, that the reusable module 206 is a certified component, that the reusable module 206 has been properly recharged, and that the reusable module 206 is within the allowable number of times the reusable module 206 can be safely recharged. The system can also include information on cartridge size or specific performance information for the reusable module 206. Performance information can include, but is not limited to, efficiency of a sorbent cartridge or module in removing specific solutes from spent dialysate, or the binding capacity of specific sorbent materials within the module 206. Additional information could be cartridge size and/or specific performance information For example, information regarding variation in chemical performance parameters could be included in the RFID tag that can then be used by the system to alter system operation parameters. In other embodiments, other relevant variations in performance parameters known to those of ordinary skill used in the performance of dialysis can be used to alter the system operational parameters when using the specific module 206. The system can also determine the length of time that has elapsed since the reusable module 206 has been used.

Information on the time elapsed between uses can be important to ensure that the reusable component 206 remains in proper working order. In particular, information regarding a parameter of when the rechargeable unit was last used can be verified by the recharger to determine if too much time has elapsed. This information can be advantageously used as an expiration or time limit to avoid possible contamination from microbial or fungal growth in a recharging/reprocessing unit or step. A second RFID reader 213 can be optionally placed so that both reusable module 206 and non-reusable module 205 can be read when connected together by mating latches 216 with annular connection ring 217 and connected or inserted into the dialysis cabinet 204. Both the first reader 209 and second reader 213 can cooperatively read the required information or read independently. Furthermore, additional RFID readers can be configured into the system as needed such as where more than one reusable module is part of a sorbent cartridge. In an alternative embodiment, the RFID tags on the modules may be placed within the sorbent material. Dialyzer 211 can also have an RFID tag 212. When the dialyzer 211 is placed in the cabinet 204, the reader 213 can read the dialyzer RFID tag 212. If reader 209 is close enough to both the sorbent modules and the dialyzer to read all three RFID tags, then the second reader 213 may not be necessary. The system can confirm that the dialyzer 211 matches the patient identification, that the dialyzer 211 is certified, that the dialyzer 211 has been recharged and is ready for use, that the dialyzer 211 is within the allowable number of times the dialyzer 211 can be safely used, and that it has not been too long of a period of time between uses of the dialyzer 211. The information may be written onto a writable RFID located on the dialyzer 211. Alternatively, the readers 209 and/or 211 may transmit the identification and use information to a central database (not shown) that can track the usage of each of the components. In this embodiment, the RFID tags do not need to be writable, and may only contain identification information. The RFID tags can be disposed on any convenient part of the component including both the exterior and interior of the component.

During or after dialysis, the writable RFID tags or system database can be updated. The system can signal the patient's RFID tag 202 of the current prescription and date of the dialysis session. The RFID tag 208 on non-reusable module 205 can be updated to show that the non-reusable module 205 has been used. The RFID tag 207 on reusable module 206 can be updated to show that the reusable module 206 has been used, and that the reusable module 206 is currently not recharged. The RFID tag 212 on dialyzer 211 can also be updated to show that the dialyzer 211 has been used and that the dialyzer 205 is currently useable.

After the dialysis is complete, the rechargeable components, such as reusable sorbent cartridge 206 may be taken from the dialysis machine 214 to a recharger 215. Before recharging, the recharger 215 can read the RFID tag 207 on the reusable module 206 to confirm that the reusable module 206 is in a used state, and that the reusable module 206 is within the number of times that the reusable module 206 can be safely recharged. The module 206 can be recharged, and the recharger 215 can write to the RFID tag 207 the date the reusable module 206 was recharged and any other information. Alternatively, the RFID tag 207 may only contain identification information and the recharger can transmit the date the component was recharged and any other information to a central database (not shown). The reusable module 206 can then be returned and is capable of being used in the next dialysis session.

Figure 24:
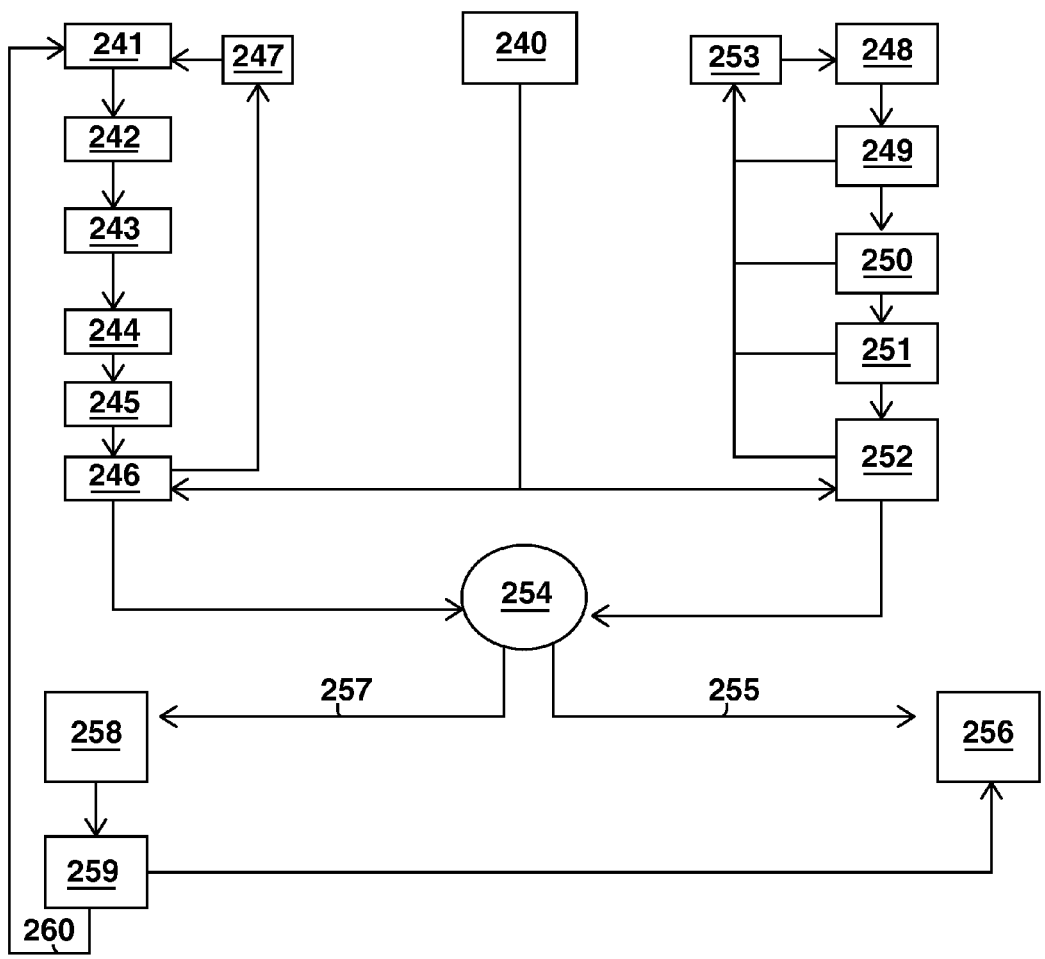
FIG. 24 shows a flow chart describing the steps of utilizing the dialysis authentication system.

The process is shown schematically in the flow chart in FIG. 24. The left side of the flow chart corresponds to a reusable component, whereas the right side of the flow chart corresponds to a non-reusable component. The patient's identification component can be read by the system at block 240. An authentication device affixed to a reusable component can be read at block 241. The system can determine whether the reusable component is a certified component 242. If the component is certified, the system can determine whether the reusable component has been properly recharged 243. Next, the system can determine whether the reusable component is still within the allowable number of uses and/or recharges and whether it has been too long since the last use of the reusable component 244. Next the system can determine whether the reusable component is within the expiration date for the component 245. Finally, the system can determine whether the component matches the patient specific unique identifier 246. If the answer to any of the inquiries is negative, a different part must be used 247, which can then be read by the reader 241. If the answer to each of the inquiries is positive, the component may be used in a dialysis session 254. The information to each of the inquiries may be stored on a memory device that is integrated into authentication component as described above, or alternatively, the reader can communicate with a database that has the information stored.

An authentication device affixed to a non-reusable component can be read at block 248. The system can determine whether the non-reusable component is a certified component 249. Next, the system can determine whether the non-reusable component has been previously used 250. The system can next determine whether the non-reusable component is within the expiration date 251. Finally, the system can determine whether the non-reusable component matches the patient specific unique identifier 252. If the answer to any of the inquiries is negative, a different part must be used 253, which can then be read by the reader 248. If the answer to each of the inquiries is positive, the non-reusable component may be used in a dialysis session 254. Again, the information may be stored in a memory device integrated with the authentication component, or the information may be stored in a database in communication with the reader.

After the dialysis session has started, the writer can write to the authentication component that the non-reusable component has been used 255. After dialysis the component may then be discarded 256. In an alternative embodiment, the system can update a database external to the authentication component that the non-reusable component has been used.

Also after the dialysis session begins, the writer can write to the authentication component on the reusable component that the component has been used 257. The writer may also include information such as the date the component was used or performance data from the dialysis session. After the dialysis session has ended, the authentication component on reusable component can be read by the recharger 258. The recharger can determine whether the reusable component has reached the maximum allowable number of recharges 259. If the reusable component has reached the maximum number of recharges, the recharger can write to the authentication component that the component has reached the end of the component's useful life and can be discarded 256. If the reusable component has not reached the end of its useful life, then the reusable module can be recharged and made ready for reuse 260. In other embodiments, the recharger or dialysis system can write to the authentication component, or database, other information, such as performance data for the component.

It will be apparent to one skilled in the art that various combinations and/or modifications and variations can be made in the dialysis system depending upon the specific needs for operation. Features illustrated or described as being part of one embodiment may be used on another embodiment to yield a still further embodiment.

We claim:

1. A dialysis authentication system comprising:
    a sorbent cartridge containing one or more sorbent materials;
    a recharger for recharging one or more sorbent materials within the sorbent cartridge;
    at least one authentication component affixed on any one or both of the sorbent cartridge and the recharger; and
    a processor monitoring any one or more features selected from the group consisting of: whether the sorbent cartridge has been recharged, a number of times the sorbent cartridge has been recharged, a sorbent cartridge-specific unique identifier, usage of the sorbent cartridge, a number of times the sorbent cartridge is disconnected and reconnected to the system, contents of the sorbent cartridge, a length of time between uses of the sorbent cartridge, usage of a counterfeit sorbent cartridge, a product history of the sorbent cartridge, and combinations thereof.

2. The dialysis authentication system of claim 1, further comprising a dialyzer.

3. The dialysis authentication system of claim 1, wherein the sorbent cartridge comprises at least one reusable module.

4. The dialysis authentication system of claim 1, wherein the authentication component is any one or more selected from the group consisting of a radio-frequency identification marker, a bar code, a one-wire security component, and a wireless authentication component.

5. The dialysis authentication system of claim 1, further comprising a memory device.

6. The dialysis authentication system of claim 1, further comprising a reader to read the authentication component.

7. The dialysis authentication system of claim 1, further comprising a writer to write to the authentication component.

8. The dialysis authentication system of claim 1, wherein the authentication component includes one or more selected from the group consisting of:
    A. a sorbent cartridge-specific or recharger-specific unique identifier;
    B. a manufacturer-specific unique identifier;
    C. a user-specific unique identifier; and
    D. an expiration date corresponding to the sorbent cartridge to which the authentication component is affixed.

9. The dialysis authentication system of claim 8, wherein the processor correlates the sorbent cartridge-specific or recharger-specific identifier with at least one or both of
    A. the manufacturer-specific unique identifier; and
    B. the user-specific unique identifier.

10. The dialysis authentication system of claim 1, wherein the processor monitors one or more selected from the group consisting of
    A. usage of the sorbent cartridge;
    B. the number of times the sorbent cartridge is disconnected and reconnected to the system;
    C. contents of the sorbent cartridge; and
    D. a length of time between uses of the sorbent cartridge.

11. The dialysis authentication system of claim 1, wherein the authentication component detects the usage of a counterfeit sorbent cartridge.

12. The dialysis authentication system of claim 11, wherein the authentication component disables the usage of the counterfeit sorbent cartridge.

13. The dialysis authentication system of claim 1, further comprising a memory device to determine the product history of the sorbent cartridge.

14. The dialysis authentication system of claim 1, wherein the authentication component is built into any one or both of the sorbent cartridge and the recharger.

15. The dialysis authentication system of claim 6 comprising more than one reader.

16. The dialysis authentication system of claim 13, wherein the memory device is one or both of a memory component integrated with the authentication component, and a memory component separate from the authentication component.

17. The dialysis authentication system of claim 13, wherein the memory device comprises a database to track one or more sorbent cartridge.

18. The dialysis authentication system of claim 1, wherein the authentication component is placed inside the sorbent cartridge.

19. The dialysis authentication system of claim 13, wherein the system determines how many times the sorbent cartridge has been used.

20. The dialysis authentication system of claim 19, wherein the system alerts a user if the sorbent cartridge has met one or more of the following conditions:
    A. has been used more than a pre-set number of times;
    B. has reached an expiration date of the sorbent cartridge; and
    C. the length of time between uses of the sorbent cartridge is greater than a pre-set length of time.

21. The dialysis authentication system of claim 1, wherein the authentication component includes information on whether the sorbent cartridge has been recharged.

22. The dialysis authentication system of claim 1, wherein the authentication component includes information on whether the sorbent cartridge has been previously used.

23. The dialysis authentication system of claim 1, wherein the authentication component includes information on the last use date of any one or more of the sorbent cartridge, the recharger and the processor.

24. The dialysis authentication system of claim 13, wherein the memory device tracks performance data of any one or more of the sorbent cartridge, the recharger and the processor.

25. The dialysis authentication system of claim 6, wherein the authentication component requires electrical contact with the reader for the authentication component to communicate with the reader; and a spring is placed on the sorbent cartridge such that when the sorbent cartridge is attached in a fluid flow path, the spring causes the authentication component to come into electrical contact with the reader.

26. The dialysis authentication system of claim 6, wherein the reader is affixed to the recharger.

27. The dialysis authentication system of claim 1, wherein the authentication component includes performance information for the sorbent cartridge.

28. The dialysis authentication system of claim 1, wherein the recharger reads the authentication component and determines whether the sorbent cartridge has reached a maximum allowable number recharges.

29. The dialysis authentication system of claim 1, wherein the recharger writes data to the authentication component selected from the group of database information and performance data for the sorbent cartridge.

30. The dialysis authentication system of claim 1, wherein the sorbent cartridge comprises a first module and a second module detachable from each other, the first module having a first sorbent material and the second module having a second sorbent material.

31. The dialysis authentication system of claim 30, further comprising a first connector connectable to the first module and the recharger wherein the recharger recharges the first sorbent material inside of the first module while the first module is detached from the second module.

32. The dialysis authentication system of claim 30, further comprising a second connector connectable to the second module and the recharger wherein the recharger recharges the second sorbent material inside of the second module while the second module is detached from the first module.

33. The dialysis authentication system of claim 1, wherein the sorbent cartridge has a modular design containing one or more sorbent materials dispersed across at least two different modules wherein the modules are connectable to form a unitary body.

34. The dialysis authentication system of claim 1, wherein the recharger recharges the one or more sorbent materials in-line within a module of the sorbent cartridge.

* * * * *